US011369321B2

(12) United States Patent
Kwan

(10) Patent No.: US 11,369,321 B2
(45) Date of Patent: **\*Jun. 28, 2022**

(54) MONITORING AND TRACKING SYSTEM, METHOD, ARTICLE AND DEVICE

(71) Applicant: Kevin Kwan, Lake Forest Park, WA (US)

(72) Inventor: Kevin Kwan, Lake Forest Park, WA (US)

(\*) Notice: Subject to any disclaimer, the term of this patent is extended or adjusted under 35 U.S.C. 154(b) by 21 days.

This patent is subject to a terminal disclaimer.

(21) Appl. No.: 16/925,845

(22) Filed: Jul. 10, 2020

(65) Prior Publication Data

US 2020/0337651 A1 Oct. 29, 2020

Related U.S. Application Data

(63) Continuation of application No. 16/455,600, filed on Jun. 27, 2019, now Pat. No. 10,736,582, which is a continuation of application No. PCT/CN2017/119937, filed on Dec. 29, 2017.

(Continued)

(51) Int. Cl.
*G08B 23/00* (2006.01)
*A61B 5/00* (2006.01)
(Continued)

(52) U.S. Cl.
CPC .............. *A61B 5/746* (2013.01); *A61B 5/117* (2013.01); *A61B 5/14532* (2013.01); *G16H 20/13* (2018.01); *G16H 40/67* (2018.01)

(58) Field of Classification Search
CPC ..... A61B 5/746; A61B 5/117; A61B 5/14532; G16H 20/13; G16H 40/67
See application file for complete search history.

(56) References Cited

U.S. PATENT DOCUMENTS 6,812,840 B2 11/2004 Gehlot et al.
8,249,526 B2 8/2012 Yao
(Continued)

FOREIGN PATENT DOCUMENTS

CN 101771742 A 7/2010
CN 102755194 A 10/2012
(Continued)

OTHER PUBLICATIONS

International Search Report and Written Opinion dated Mar. 27, 2018, for International Application No. PCT/CN2017/119937, 6 pages.

*Primary Examiner* — Toan N Pham
(74) *Attorney, Agent, or Firm* — Seed IP Law Group LLP

(57) ABSTRACT

A monitoring system includes one or more monitoring devices configured to detect conditions related to a monitored person and an artificial intelligence module configured to analyze historical information related to conditions of the monitored person and current information related to conditions of the monitored person and determine whether to generate an alert signal based on the analysis. The artificial intelligence module may also be configured to update the historical information related to the conditions of the monitored person based on the current information and responses to the alert signals. The system includes a moveable sensor and a monitored-person identification subsystem.

20 Claims, 15 Drawing Sheets

Related U.S. Application Data

(60) Provisional application No. 62/440,268, filed on Dec. 29, 2016, provisional application No. 62/599,690, filed on Dec. 16, 2017.

(51) Int. Cl.
| | |
|---|---|
| *G16H 40/67* | (2018.01) |
| *G16H 20/13* | (2018.01) |
| *A61B 5/117* | (2016.01) |
| *A61B 5/145* | (2006.01) |

(56) References Cited

U.S. PATENT DOCUMENTS

| | | | |
|---|---|---|---|
| 8,346,391 | B1 | 1/2013 | Anhalt et al. |
| 8,466,795 | B2 | 6/2013 | Hoffman et al. |
| 10,736,582 | B2* | 8/2020 | Kwan ................. A61B 5/00 |
| 2002/0109595 | A1 | 8/2002 | Cairo et al. |
| 2010/0052897 | A1* | 3/2010 | Allen .................. A61B 5/411 |
| | | | 340/539.12 |
| 2012/0053472 | A1 | 3/2012 | Tran |
| 2012/0056746 | A1 | 3/2012 | Kaigler et al. |
| 2015/0317809 | A1 | 11/2015 | Chellappan et al. |
| 2016/0166156 | A1* | 6/2016 | Yuen .................. A61B 5/0816 |
| | | | 340/573.1 |
| 2021/0052221 | A1* | 2/2021 | Panneer Selvam .... A61B 5/681 |

FOREIGN PATENT DOCUMENTS

| | | |
|---|---|---|
| CN | 104771177 A | 7/2015 |
| CN | 105615850 A | 6/2016 |
| CN | 106054083 A | 10/2016 |
| WO | 2013023067 A2 | 2/2013 |

* cited by examiner

MONITORING AND TRACKING SYSTEM, METHOD, ARTICLE AND DEVICE

BACKGROUND

Technical Field

The present disclosure relates to systems, methods and articles for monitoring and tracking systems.

Description of the Related-Art

Monitoring and tracking systems may employ a manual or mechanically triggered signal to indicate a monitored premises or a monitored person is in danger or needs assistance. For example, a button on a necklace may be pressed to generate a signal indicating a person needs assistance, or a window may be fitted with a detector to detect opening of the window. The signal may trigger a remote alarm.

BRIEF SUMMARY

In an embodiment, a monitoring system comprises: at least one device configured to generate signals indicative of a safety status of an individual; and a safety status monitoring module configured to receive the signals indicative of the safety status of the individual and to determine based on the received signals whether to generate a safety alert regarding the safety status of the individual and, when it is determined to generate a safety alert, to cause the safety alert to be generated and transmitted. In an embodiment, the at least one device includes one or more devices selected from: a location sensor; a thermal sensor; a health status monitoring device; an image capture device; and a video capturing device. In an embodiment, the at least one device is communicatively coupled with remote servers configured to implement the safety status monitoring module. In an embodiment, the at least one device includes a device configured to perform voice communications. In an embodiment, the device configured to perform voice communications is configured to be activated in response to a determination to activate a safety alert.

In an embodiment, a method comprises: monitoring indications of a safety condition of an individual; and generating a safety alert based on the monitored indications. In an embodiment, the monitoring indications includes monitoring at least one device selected from: a location sensor; a thermal sensor; a health status monitoring device; and a video capturing device. In an embodiment, the at least one device is communicatively coupled with remote servers configured to perform the monitoring and the generating. In an embodiment, the method comprises initiating voice communications in response to a safety alert. In an embodiment, a non-transitory computer-readable medium contents are configured to cause one or more devices to perform one or more methods disclosed herein.

In an embodiment, a system comprises: means for monitoring indications of a safety condition of an individual; and means for generating a safety alert based on the monitored indications.

In an embodiment, a safety monitoring system comprises: one or more sensors configured to generate at least one signal indicative of a current condition related to a safety status of a person; and one or more processing devices configured to: determine a safety status of the person based on the at least one signal indicative of the current condition and stored information related to the safety status of the person; update the stored information related to the safety status of the person based on the at least one signal indicative of the current condition; and when the determined safety status indicates the person may be in danger: initiate one or more actions based on the determined safety status; monitor responses to the one or more initiated actions; and update the stored information related to the safety status of the person based on the monitored responses. In an embodiment, the one or more initiated actions comprise one or more of: generating an alert signal to the person; transmitting a signal to a remote server; and generating an alert message based on stored contact information. In an embodiment, the one or more sensors include at least one of: a location sensor; a thermal sensor; a health status monitoring device; a motion sensor; a facial recognition sensor; and a video capturing device. In an embodiment, a sensor may sense one or more of a temperature, a pulse, a breathing state (e.g. breathing rate, breathing depth), a heart rate, motion, objects, images, etc. In an embodiment, the safety monitoring system comprises a device configured to perform voice communications. In an embodiment, the stored information comprises property identifiers indicative of conditions and the one or more processing devices comprise an artificial intelligence module configured to compare the at least one signal to the stored property identifiers and to determine the safety status of the person based on the comparison. In an embodiment, the determining the safety status comprises determining a position of a property identifier on a characteristic property-identifier curve based on the at least one signal. In an embodiment, the curve is a Bell curve. In an embodiment, the characteristic Bell curve is based on stored property identifiers indicative of the characteristic. In an embodiment, the characteristic Bell curve is related to one or more of: an object identifier; a location identifier; a position identifier; a time identifier; a sound identifier; a motion identifier; a physical status identifier; and an emotional identifier. In an embodiment, the determining the safety status comprises determining whether the position is within one or more threshold deviations from a mean of the Bell curve. In an embodiment, the stored information includes an initial data set and updating the stored information comprises adding data to the initial data set. In an embodiment, the initial data set is a generic data set not specific to the person. In an embodiment, one or more of the sensors may be mounted on a mobile device (e.g., a robot), which, in operation, identifies a person to monitor (e.g., using one or more sensors and stored identification information, such as facial recognition data, physical shape data, other personal data) and follows the identified monitored person as the monitored person moves around. In an embodiment, the robot may have a defined area in which to follow the monitored person around (e.g., inside a house or an apartment).

In an embodiment, the monitoring system includes a camera which, in operation, follows a monitored body around a house. In an embodiment, the camera uses a wide angle lens. In an embodiment, the system settings are selected (such as a lens to use, focus settings, sensing time frames) to use based on monitoring conditions or desired characteristics to monitor (e.g., distance to the monitored person, data to be sensed (e.g., temperature, body position, breathing rate, breathing depth, heart rate, etc.)). In an embodiment, the camera is mounted to a moveable support (e.g., a robot), which, in operation, moves or follows the monitored person based on detected motion and/or other information.

In an embodiment, the system comprises one or more motion sensors and one or more thermal sensors, wherein in operation, the thermal sensors are activated and deactivated based on information sensed by the motion sensors. In an embodiment, the system comprises one or more motion sensors and one or more image sensors, wherein in operation, the image sensors are activated and deactivated based on information sensed by the motion sensors.

In an embodiment, the system identifies a person to be monitored based on one or more of: facial recognition techniques, body temperature, body type/shape, other biological indicators, etc. This facilitates identifying a person to monitor when more than one person is in a monitored location. For example, a house having more than one occupant when only one occupant is to be monitored (e.g., an occupant having diabetes or other health issues who may be unable to summon assistance in a medical emergency).

In an embodiment, the system includes a robot which follows a person to be monitored (e.g., a senior, a patient) and includes one or more of an image sensor which senses images at a wide angle or selectable angles, an infrared sensor, infrared beams, infrared night vision systems, facial recognition subsystems, etc. to facilitate identifying and monitoring the person to be monitored. In an embodiment, the system may provide medication to the patient, monitor patient medication intake, measure blood pressure, measure glucose content, measure heart rate, etc. (with or without using a robot in an embodiment having a robot).

In an embodiment, a system comprises a combination of mounted sensors (e.g., a camera or motion sensor mounted on a wall) and mobile sensors (e.g., one or more sensors carried by a person to be monitored, one or more sensors mounted to one or more robots). For example, an entry way or staircase may have a mounted sensor, a first floor may have a first robot, a second floor may a second robot, etc., and various combinations thereof.

In an embodiment, a method comprises: receiving at least one signal indicative of a current condition related to a safety status of a person; determining, using at least one processing device, a safety status of the person based on the at least one signal indicative of the current condition and stored information related to the safety status of the person; updating, using the at least one processing device, the stored information related to the safety status of the person based on the at least one signal indicative of the current condition; and when the determined safety status indicates the person may be in danger: initiating one or more actions based on the determined safety status; monitoring responses to the one or more initiated actions; and updating the stored information related to the safety status of the person based on the monitored responses. In an embodiment, the one or more initiated actions comprise one or more of: generating an alert signal to the person; transmitting a signal to a remote server; and generating an alert message based on stored contact information. In an embodiment, the at least one signal includes at least one of: a signal indicative of a location of the person; a signal indicative of a temperature; a signal indicative of a health status of the person; and an imaging signal. In an embodiment, the stored information comprises property identifiers indicative of conditions and the at least one processing device comprises an artificial intelligence module configured to compare the at least one signal to the stored property identifiers and to determine the safety status of the person based on the comparison. In an embodiment, the determining the safety status comprises determining a position of a property identifier on a characteristic Bell curve based on the at least one signal. In an embodiment, the characteristic Bell curve is based on stored property identifiers indicative of the characteristic. In an embodiment, the characteristic Bell curve is related to one or more of: an object identifier; a location identifier; a position identifier; a time identifier; a sound identifier; a motion identifier; a physical status identifier; and an emotional identifier. In an embodiment, a non-transitory computer-readable medium contents configure a safety monitoring system to perform a method, the method comprising: receiving at least one signal indicative of a current condition related to a safety status of a person; determining a safety status of the person based on the at least one signal indicative of the current condition and stored information related to the safety status of the person; updating the stored information related to the safety status of the person based on the at least one signal indicative of the current condition; and when the determined safety status indicates the person may be in danger: initiating one or more actions based on the determined safety status; monitoring responses to the one or more initiated actions; and updating the stored information related to the safety status of the person based on the monitored responses.

In an embodiment, a system comprises: means for generating at least one signal indicative of a current condition related to a safety status of a person; means for determining a safety status of the person based on the at least one signal indicative of the current condition and stored information related to the safety status of the person; means for updating the stored information related to the safety status of the person based on the at least one signal indicative of the current condition; and means for, when the determined safety status indicates the person may be in danger, initiating one or more actions based on the determined safety status; monitoring responses to the one or more initiated actions; and updating the stored information related to the safety status of the person based on the monitored responses.

In an embodiment, a safety monitoring system comprises: a plurality of sensors configured to generate signals indicative of a current condition related to a safety status of a person; and one or more processing devices coupled to the plurality of sensors and configured to: determine a safety status of the person based on the signals indicative of the current condition and stored information related to the safety status of the person; update the stored information related to the safety status of the person based on the signals indicative of the current condition; and in response to the determined safety status indicating the person may be in danger: initiate one or more actions based on the determined safety status; monitor responses to the one or more initiated actions; and update the stored information related to the safety status of the person based on the monitored responses. In an embodiment, the one or more initiated actions comprise: generating an alert signal to the person; transmitting a signal to a remote server; generating an alert message based on stored contact information; or combinations thereof. In an embodiment, the plurality of sensors include: a location sensor; a thermal sensor; a health status monitoring device; a radar sensor; a video capturing device; or combinations thereof.

BRIEF DESCRIPTION OF THE SEVERAL VIEWS OF THE DRAWING(S)

DETAILED DESCRIPTION

Figure 1:
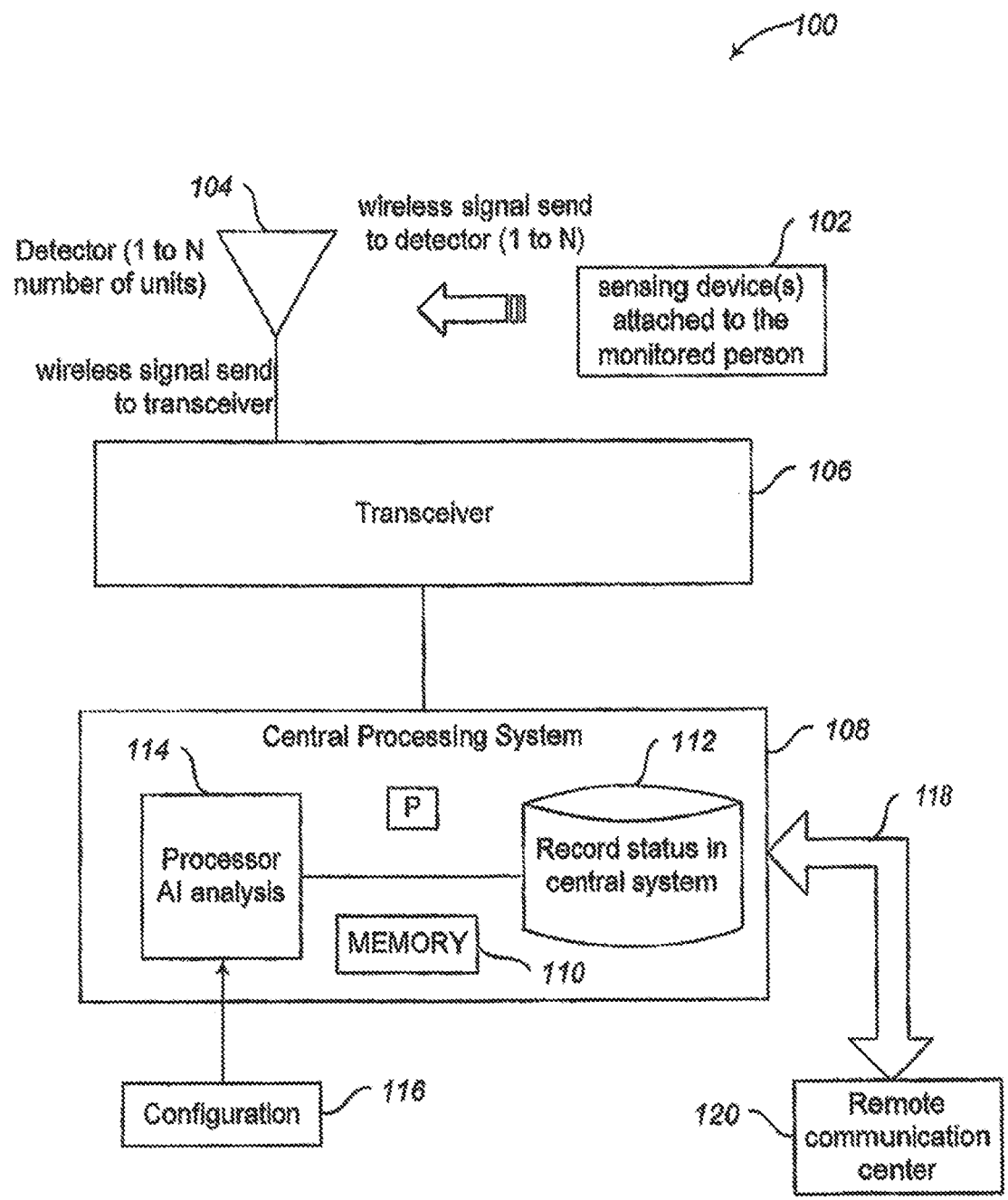
FIG. 1 is a functional block diagram of an embodiment of an environment suitable for providing monitoring and tracking services.

In the following description, certain details are set forth in order to provide a thorough understanding of various embodiments of devices, systems, methods and articles. However, one of skill in the art will understand that other embodiments may be practiced without these details. In other instances, well-known structures and methods associated with, for example, mobile devices such as smart phones, GPS devices and systems, computing systems, telecommunication networks, web browsers, web servers, etc., have not been shown or described in detail in some figures to avoid unnecessarily obscuring descriptions of the embodiments.

Unless the context requires otherwise, throughout the specification and claims which follow, the word "comprise" and variations thereof, such as "comprising," and "comprises," are to be construed in an open, inclusive sense, that is, as "including, but not limited to."

Reference throughout this specification to "one embodiment," or "an embodiment" means that a particular feature, structure or characteristic described in connection with the embodiment is included in at least one embodiment. Thus, the appearances of the phrases "in one embodiment," or "in an embodiment" in various places throughout this specification are not necessarily referring to the same embodiment, or to all embodiments. Furthermore, the particular features, structures, or characteristics may be combined in any suitable manner in one or more embodiments to obtain further embodiments.

The headings are provided for convenience only, and do not interpret the scope or meaning of this disclosure or the claimed invention.

The sizes and relative positions of elements in the drawings are not necessarily drawn to scale. For example, the shapes of various elements and angles are not drawn to scale, and some of these elements are enlarged and positioned to improve drawing legibility. Further, the particular shapes of the elements as drawn are not necessarily intended to convey any information regarding the actual shape of particular elements, and have been selected solely for ease of recognition in the drawings.

Embodiments of systems and methods in which electronic devices such as monitoring and tracking devices are described herein.

The following discussion provides a brief, general description of a suitable computing environment in which the embodiments described herein may be implemented. Although not required, various embodiments will be described in the general context of computer-executable instructions, such as program application modules, objects, or macros being executed by one or more electronic devices, such as a monitoring and tracking device, a smart phone, a personal computer, a server, etc., and various combinations thereof. Those skilled in the relevant art will appreciate that various embodiments can be practiced with other computing system configurations, including other handheld devices, multiprocessor systems, microprocessor-based or programmable consumer electronics, networked personal computers (PCs), minicomputers, mainframe computers, virtual systems, and the like. Various embodiments can be practiced in distributed computing environments where tasks or modules are performed by remote processing devices, which are linked through a communications network. In a distributed computing environment, program modules may be located in both local and remote memory storage devices.

For people with mobility difficulties due to disability, injury, illness or cognitive impairment (Alzheimer's, dementia, memory loss, etc.), daily functioning can be a constant challenge, with serious risks and potentially deadly consequences. Naturally, friends and relatives of these people are concerned for their welfare and would like to know when help is needed.

An embodiment of a monitoring system provides a tracking and monitoring record and transmits information to the concerned relatives/parties. In an embodiment, an alert is generated and provided to designated entities, such as friends and families (concerned parties) or devices associated with such parties when there is an indication the monitored person is in a situation where assistance might be needed. These alerts can be sent to any devices that are capable of receiving electronic messages, such as computers (all kinds), cell phones, hand held devices, personal call/voice messages, pagers, etc. Concerned parties can also use any digital device to access the secure record from a datacenter, or use the Internet to access the status record of the monitored person.

In an embodiment, the monitoring system comprises various components, such as:

A) Geo system—a sensing device that tracks the monitored person's location or position;

B) Health tracking system—monitors changes in one or more of the person's basic vital signs;

C) Thermal system—a thermal image monitoring system (infrared sensor, infrared beams, infrared night vision subsystems, etc.);

i) an AI image recognition system to analyze and determine the status of the human "object" (e.g., sitting, standing, reading, fighting, fallen, crawling on the floor, etc.);

ii) a human monitoring group to determine the status of the monitored person;

D) Image system—a full video monitoring system. This includes three analytical systems:

i) an AI image recognition system to analyze and determine the status of the human "object" (e.g., sitting, standing, reading, fighting, fallen, crawling on the floor, etc.);

ii) a human monitoring group to determine the status of the monitored person;

iii) a movement detection system to detect movement of the monitored person;

E) Both Thermal and Image (e.g., video, radar, etc.) system—This system may be used when a client desires a system with both private circumstance like a bathroom and regular open area like a living room.

An embodiment may include fewer or more of components, and various combinations of components. The following describes example embodiments of these categories:

A) Geo system—detects person's location or movements within their environment, and if they try to leave a defined area.

A sensing device is attached to the monitored person. In the primary monitored location (property/residence), a different receiver will be installed to detect the person's location. This information will be recorded with a time stamp of how long they spent in each area, and sent to a central processing system where it is stored in the status database.

An "alert" notification will be sent when a person is in a dangerous situation, which is determined based on algorithm settings customized by the client. Various definitions of an alert/danger status may be employed. The definition of an alert/danger status may be different from situation to situation and from person to person, but could include conditions such as the person leaving the building or staying in bathroom for more than an hour.

Therefore, in an embodiment, the client/customer will be able to specify the parameters of what constitutes a dangerous situation, and when those conditions are met, a central processing system will send out an alert message to the necessary parties in any digital format (voice mail, phone text messages, email, SMS, IM, etc.) through any network (e.g., mobile, WAN, LAN, etc.). The scenario of when (and how long) to send the alert may be purely determined by the client. Applications running on mobile or other devices (e.g., apps running on a smart phone, smart appliances, IoT devices, etc.), may be employed to configure the system parameters, to provide sensor and activity data (e.g., stove on, refrigerator door open, etc.), to receive and respond to alerts (e.g., turning off an appliance, locking a door, turning off water, draining a tub, etc.), etc., and various combinations thereof. In an embodiment, sensors may be built into various appliances and home features and furnishings (e.g., walls, stoves, floors, bedding (e.g., mattresses, mattress covers), furniture (e.g., padding), etc., and may be configured to detect any number of conditions, such as sleeping patterns, body temperature, wake-up time, accidents (e.g., falling out of bed), etc.

The sensing device could be anything attached to the body, such as an implant chip under the skin, a bracelet, a necklace, an electronic coding device glued to fingernail or toenail, etc. In an embodiment, detection of a location of a monitored person may be performed using other data, such as thermal imaging data from one or more thermal sensors, video imaging data from one or more image capturing devices; radar or lidar imaging data from one or more radar or lidar imaging sensors; sonar data from one or more sonar imaging devices; etc.

FIG. 1 shows an embodiment of a system 100 configured to monitor a location of a person. As illustrated, the system 100 has a sensing device 102 which may be attached to the person and configured to sense a location of the person or to send out signals from which the location of the person can be determined. As illustrated, the sensing device 102 sends out a signal to one or more detectors 104, for example, periodically. The sensing device 102 may comprise one or more antennas for communicating with the detectors 104. The detectors 104 receive the signals from the sensor 102 and forward the signals to a transceiver 106 which is communicatively coupled to a central processing system 108. The central processing system 108 has one or more processors P, one or more memories 110 and one or more data bases, such as a database 112 indicating a record status in the central processing system 108, and may be configured to process the signals to determine the person's location at various time periods and based on the person's location at the various time periods, determine whether there is a likelihood the person needs assistance. The determinations may be based on other criteria and data as well as location related data, such as a time of day, accrued or snapshots of time in a particular location (e.g., too much time in the bathroom in a single time period, too much cumulative time in a bathroom in a window of time, too little time in the bathroom, too much time elapsed between visits to a location such as the kitchen, etc.) day of the week, other sensor signals (such as signals indicative of a vital sign, temperature, breathing rate, breathing depth, heart rate, blood sugar level), etc. The various communication links may be wired or wireless. The central processing system 108 includes an artificial intelligence processor 114 configured to implement learning algorithms as discussed in more detail elsewhere herein. The central processing system 108 also includes an interface 116 that may be employed to configure the system 100, for example by providing initial parameters, configuration information, override commands, etc., to the central processing system 108. As illustrated, the system 100 comprises a network 118 configured to communicatively couple the system 100 to one or more remote communication centers 120. The network 118 may be configured to provide secure communications.

Figure 2:
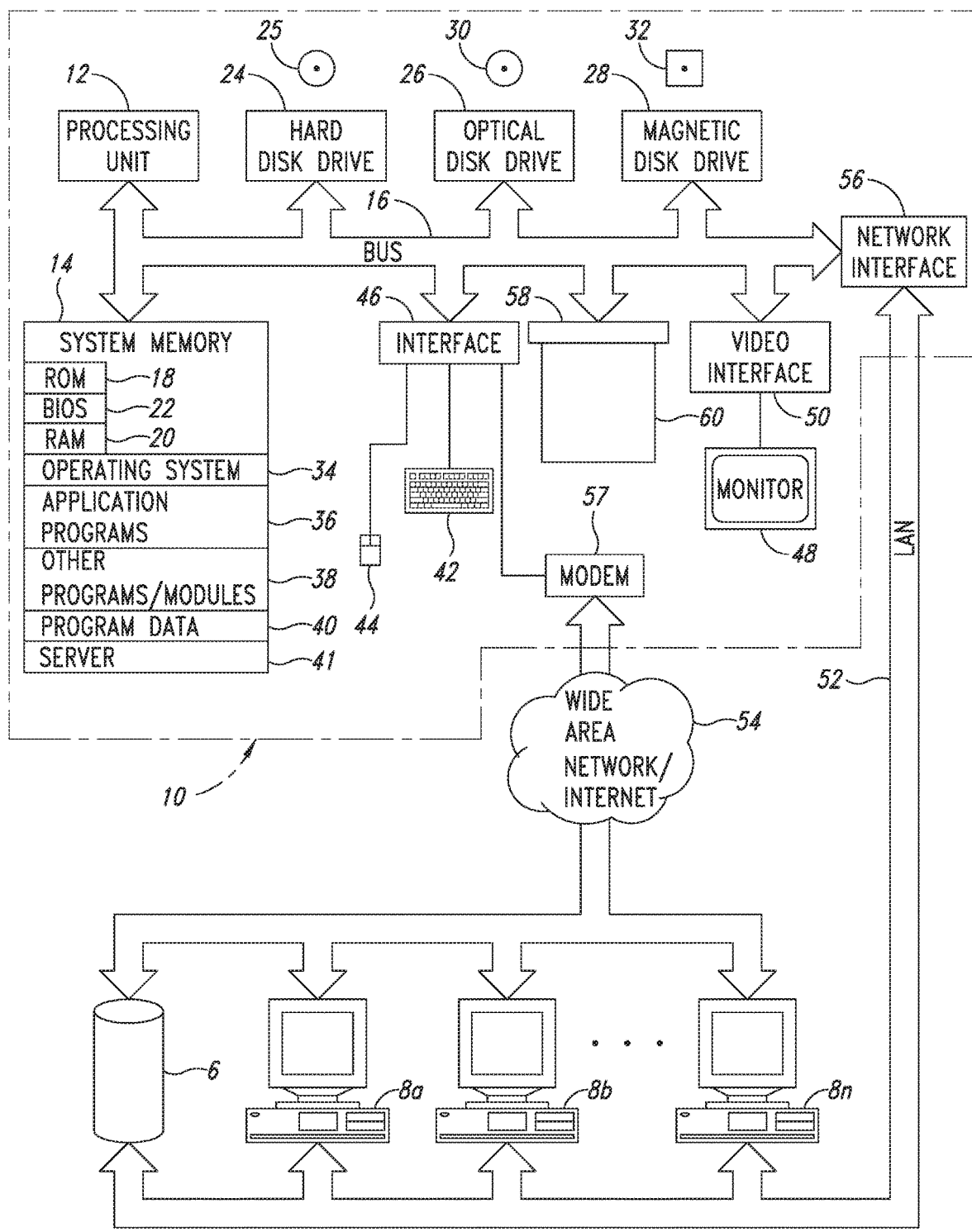
FIG. 2 is a functional block diagram of an embodiment of an environment suitable for providing monitoring and tracking services.

FIG. 2 shows an embodiment of an environment 200 that may be employed to monitoring and tracking as described herein. The environment 200 includes a computing system 10. For example, the computing system 10 may be configured as a tracking and monitoring system, a host server, such as a security services server, a communications server, etc. The computing system 10 may, for example, be operated by a service providing monitoring services and related goods and services to a consumer, by a consumer purchasing such goods or services from a service, by a vendor, such as a telecom service provider, an Internet service provider), etc. The computing system 10 may take the form of any of the variety of types discussed above, which may run a networking client, for example a server, a Web browser, etc. The computing system 10 comprises a processor unit 12, a system memory 14 and a system bus 16 that couples various system components including the system memory 14 to the processing unit 12. The processing unit 12 may be any logical processing unit, such as one or more central processing units (CPUs), digital signal processors (DSPs), application-specific integrated circuits (ASIC), state machine, fuzzy-logic modules, etc., and various combinations thereof. Unless described otherwise, the construction and operation of the various blocks shown in FIG. 2 are of conventional design. As a result, such blocks need not be described in further detail herein, as they will be understood by those skilled in the relevant art.

The system bus 16 can employ any known bus structures or architectures, including a memory bus with memory controller, a peripheral bus, and/or a local bus. The system memory 14 includes read-only memory ("ROM") 18 and random access memory ("RAM") 20. A basic input/output system ("BIOS") 22, which can form part of the ROM 18, contains basic routines that help transfer information between elements within the computing system 10, such as during startup.

The computing system 10 also includes one or more spinning media memories such as a hard disk drive 24 for reading from and writing to a hard disk 25, and an optical disk drive 26 and a magnetic disk drive 28 for reading from and writing to removable optical disks 30 and magnetic disks 32, respectively. The optical disk 30 can be a CD-ROM, while the magnetic disk 32 can be a magnetic floppy disk or diskette. The hard disk drive 24, optical disk drive 26 and magnetic disk drive 28 communicate with the processing unit 12 via the bus 16. The hard disk drive 24, optical disk drive 26 and magnetic disk drive 28 may include interfaces or controllers coupled between such drives and the bus 16, as is known by those skilled in the relevant art, for example via an IDE (Integrated Drive Electronics) interface. The drives 24, 26 and 28, and their associated computer-readable media, provide nonvolatile storage of computer-readable instructions, data structures, program modules and other data for the computing system 10. Although the depicted computing system 10 employs hard disk 25, optical disk 30 and magnetic disk 32, those skilled in the relevant art will appreciate that other types of spinning media memory computer-readable media may be employed, such as, digital video disks (DVD), Bernoulli cartridges, etc. Those skilled in the relevant art will also appreciate that other types of computer-readable media that can store data accessible by a computer may be employed, for example, non-spinning media memories such as magnetic cassettes, flash memory cards, USB sticks, solid state memories, RAMs, ROMs, smart cards, etc.

Program modules can be stored in the system memory 14, such as an operating system 34 (for example, Windows, Android, Mac OS, 10S, etc), one or more application programs 36, other programs or modules 38, and program data 40. The system memory 14 also includes a server 41 for permitting the computing system 10 to exchange data with sources such as Websites of the Internet, corporate intranets, or other networks, as well as other server applications on server computers. The server 41 may be markup language based, such as hypertext markup language (HTML), and operate with markup languages that use syntactically delimited characters added to the data of a document to represent the structure of the document, etc.

While shown in FIG. 2 as being stored in the system memory 14, the operating system 34, application programs 36, other program modules 38, program data 40 and server 41 can be stored on the hard disk 25 of the hard disk drive 24, the optical disk 30 and the optical disk drive 26 and/or the magnetic disk 32 of the magnetic disk drive 28, a solid state memory, etc. A user can enter commands and information to the computing system 10 through input devices such as a keypad or keyboard 42 and a pointing device such as a mouse 44. Other input devices can include a microphone, joystick, game pad, scanner, touch screen, card reader, chip reader, etc. These and other input devices as illustrated are connected to the processing unit 12 through an interface 46 such as a serial port interface that couples to the bus 16, although other interfaces such as a parallel port, a game port or a universal serial bus (USB) can be used. A display or monitor 48 or other display devices may be coupled to the bus 16 via video interface 50, such as a video adapter. The computing system 10 can include other output devices such as speakers, printers, etc.

The computing system 10 can operate in a networked environment using logical connections to one or more repositories 6 and/or other computing systems 8a-8n. The computer system 10 may employ any known means of communications, such as through a local area network (LAN) 52 or a wide area network (WAN), a telecommunications network or the Internet 54. Such networking environments are well known and may include, for example, any type of telecommunications network or other network, such as CDMA, OFDMA, GSM, WiMAX, VoIP, WiFi, Internet Protocol, various IEEE standard protocols, etc.

When used in a LAN networking environment, the computing system 10 may be coupled to the LAN 52 through an adapter or network interface 56 (communicatively linked to the bus 16). When used in a WAN networking environment, the computing system 10 often includes a device, such as a modem 57, a mobile phone communication module or other device for establishing communications over the WAN/Internet 54. As illustrated, a modem 57 is shown in FIG. 2 as communicatively linked between the interface 46 and the WAN/Internet/Telecommunications network 54. In a networked environment, program modules, application programs, or data, or portions thereof, can be stored in a server computer (for example, another configured computing system similar to the computing system 10). Those skilled in the relevant art will readily recognize that the network connections shown in FIG. 2 are only some examples of establishing communication links between computers and/or other systems and devices 60, and other links may be used, including wireless links. The devices may include, for example, sensors and monitors (see FIGS. 1, 3, 5, 7 and 9).

The computing system 10 may include one or more interfaces such as slot 58 to allow the addition of devices either internally or externally to the computing system 10. For example, suitable interfaces may include ISA (Industry Standard Architecture), IDE, PCI (Personal Computer Interface) and/or AGP (Advance Graphics Processor) slot connectors for option cards, serial and/or parallel ports, USB ports (Universal Serial Bus), audio input/output (I/O) and MIDI/joystick connectors, slots for memory, credit card readers, scanners, bar code readers, RFID readers, etc., collectively referenced as 60.

The term computer-readable medium as used herein refers to any medium that participates in providing instructions to processor unit 12 for execution. Such a medium may take many forms, including but not limited to, non-volatile media, and volatile media. Non-volatile media includes, for example, hard, optical or magnetic disks 25, 30, 32, respectively. Volatile media includes dynamic memory, such as system memory 14.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, as described hereinafter, or any other medium from which a computer can read.

Various forms of computer readable media may be involved in carrying one or more sequences of one or more instructions to processor unit 12 for execution. For example, the instructions may initially be carried on a magnetic disk of a remote computer. The remote computer can load the instructions into its dynamic memory and send the instructions over a telephone line using a modem. A modem 57 local to computer system 10 can receive the data on the telephone line and use an infrared transmitter to convert the data to an infrared signal. An infrared detector coupled to the system bus 16 can receive the data carried in the infrared signal and place the data on system bus 16. The system bus 16 carries the data to system memory 14, from which processor unit 12 retrieves and executes the instructions. The instructions received by system memory 14 may optionally be stored on storage device either before or after execution by processor unit 12.

The repository 6 is a permanent storage medium for data. The repository 6 may be specific to each end user, or shared between some or all end users. For example, different services vendors or concerned parties (for example, family members or health care providers) may have separate repositories or may share repositories. The repository 6 (only one illustrated) may run on the same computing system as an application accessing the repository, or on another computing system accessible over the network 52, 54, or on a network of distributed repositories.

Embodiments of the computing system 10 of FIG. 2 may not include all of the illustrated components of the computing system 10, may contain additional components not shown in FIG. 2, and may not be configured as shown in FIG. 2. For example, a computing system 10 configured as home monitoring system (see FIG. 1), may not include an optical disk drive and may include an application specific integrated circuit or a digital signal processor (not shown) to perform one or more of the functions of the home monitoring system. In another example, a detector or transceiver may include one or more telecommunications modules to handle call processing, such as CDMA, OFDMA, GSM, etc., call processing.

Figure 3:
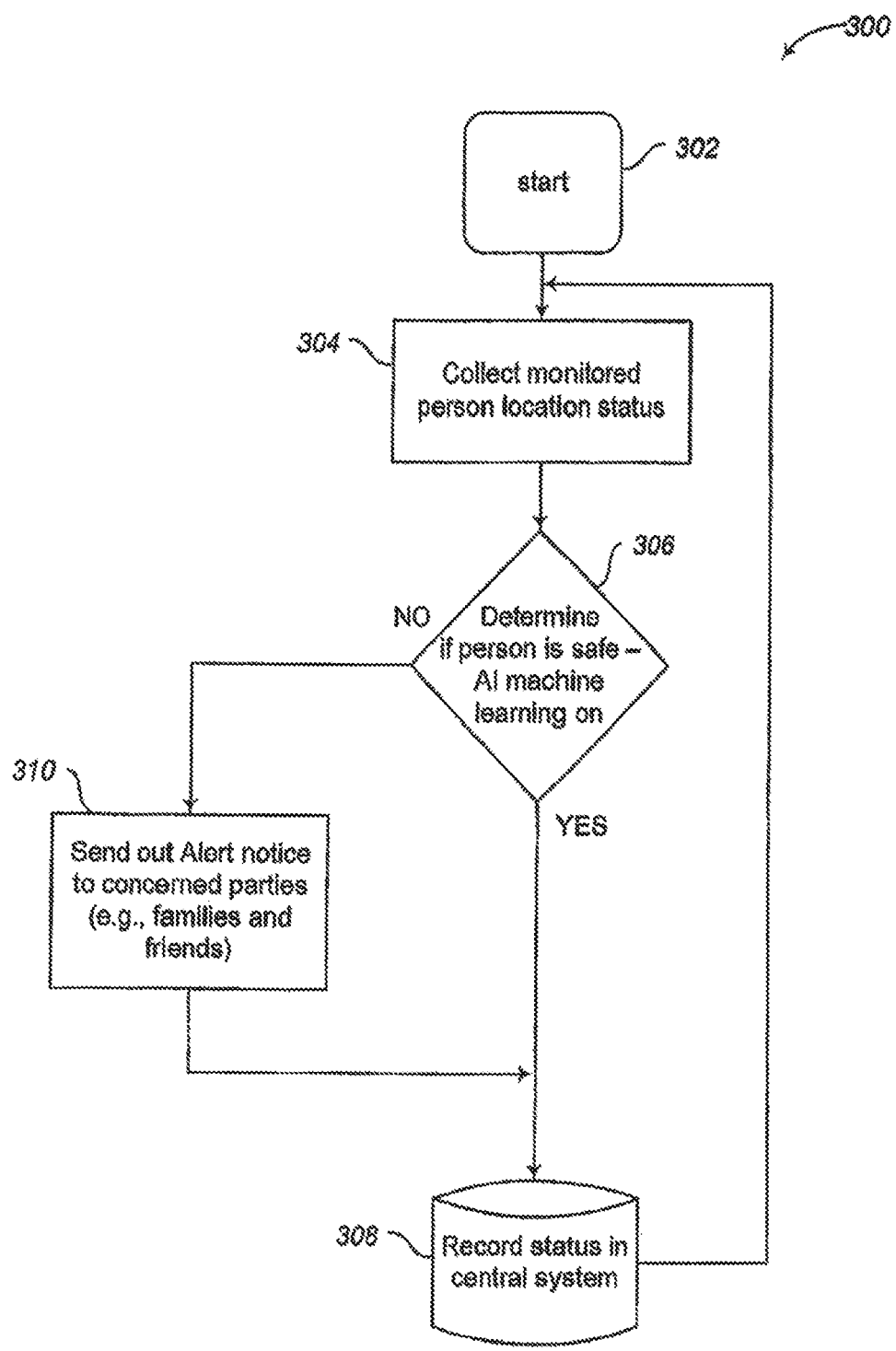
FIG. 3 is a flow diagram of a method of monitoring a location of a person.

FIG. 3 is a flow diagram of an embodiment of a method 300 of monitoring a person's location, for example to determine whether there is an indication the person may need assistance based on information related to the person's location. As illustrated, the method 300 determines whether there is an indication the person is safe or needs assistance. The method starts at block 302. At block 304, the method 300 gathers location related information and proceeds at block 306 to determine based on the gathered information whether there is an indication the person needs assistance. The determination may be based on the absence of information, the change or lack of change of the information, other information (for example, vital signs, information about the person's physical orientation, time of day, movement history), etc. Artificial intelligence algorithms may be employed to maintain (e.g., update, adjust, etc.) the criteria for determining whether the person is safe. When it is not determined that there is an indication the person needs assistance (as illustrated, when it is determined the person is safe), the method 300 proceeds to block 308 to update status information in a database, for example, to indicate that at a particular time the person is in a particular location. The method 300 proceeds from block 308 to block 304.

When it is determined at block 306 that there is an indication the person may need assistance (as illustrated, a determination the person is unsafe), the method 300 proceeds block 310 to take appropriate action in response, such as generating and transmitting alert notices to concerned parties (e.g., family and friends via designated devices), generating signals to initiate other actions (e.g., turning on lights, turning off a stove, etc.). The alert notices may provide real-time condition status levels and summary information (e.g., "Warning! Abnormal Status: living room, no movement, 24 minutes, sitting posture"; "Normal Status: living room, sitting posture"; "Dangerous!: kitchen, no movement, 18 minutes, lying posture"; etc.). The method 300 then proceeds to block 308 to update status information, as discussed above. The method 300 proceeds from block 308 to block 304. The embodiment of the system 100 of FIG. 1 and the embodiment of the system 200 of FIG. 2 may be configured to perform all or part of the method 300. Other systems (e.g., the system 400 of FIG. 4) and various combinations of systems or components thereof, may be employed to implement all or part of the method 300 of FIG. 3.

Figure 4:
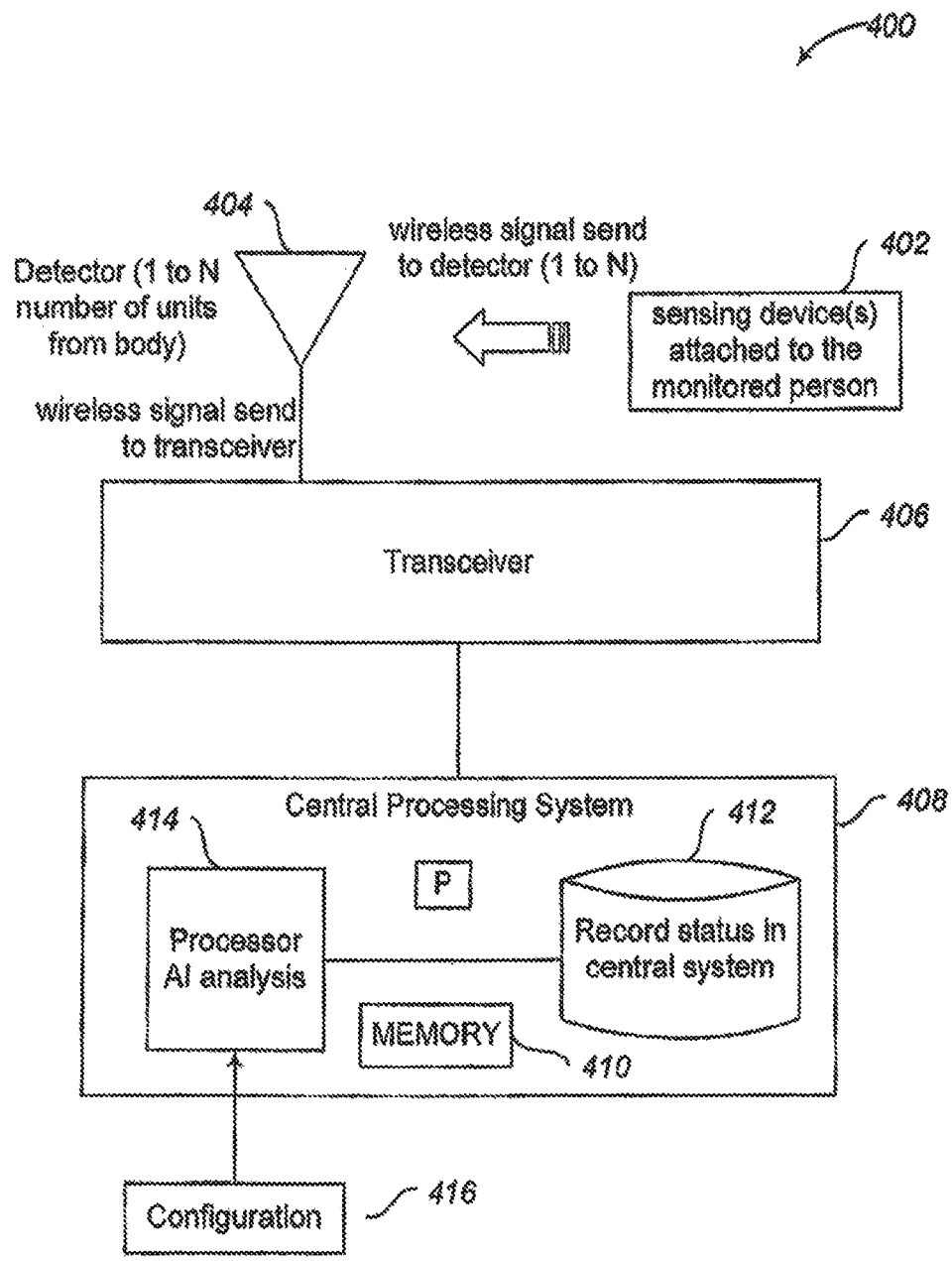
FIG. 4 is a functional block diagram of an embodiment of an environment suitable for providing monitoring and tracking services.
Figure 14:
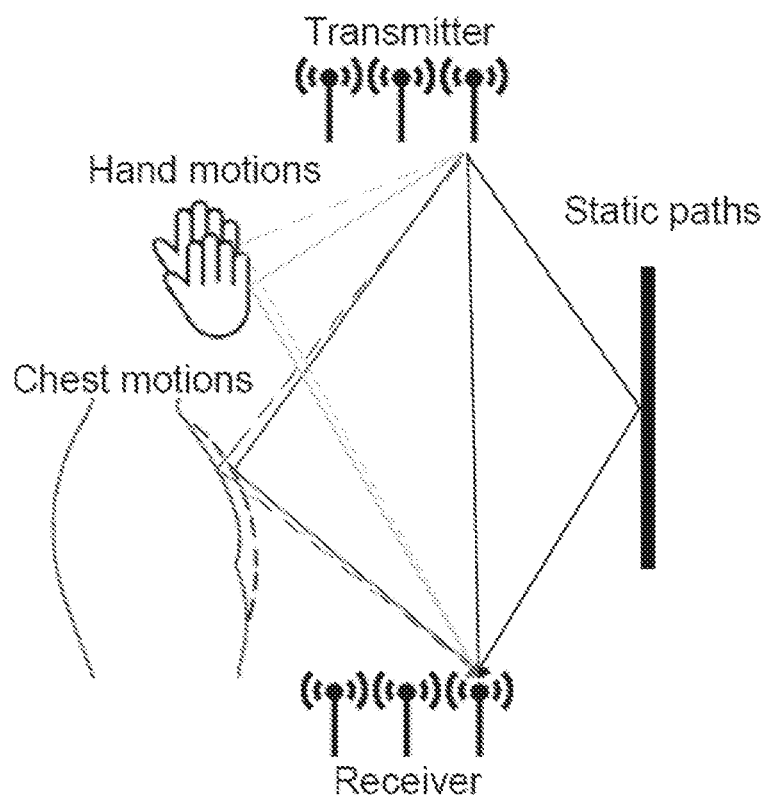
FIG. 14 is an illustration of monitoring breathing rate using remote sensing technology.

FIG. 4 shows an embodiment of a system 400 configured to monitor a health status of a person. In an embodiment, a health tracking system 400 monitors an overall health condition by tracking a range of person's vital signs. For example, a wrist-strap sensor 402 keeps track of heart/breathing rate, blood oxygen, temperature, blood pressure, etc. Data is sent to the central processing system 408, and alerts are generated if any readings change dramatically or enter a "danger zone," or are inconsistent with past behavior patterns. For example, body temperatures or changes in body temperature or characteristic body temperature histograms or other histograms (e.g., movement histograms, combined histograms) may indicate the existence of a medical emergency, such as a diabetic coma. For another example, heart/breathing rate is monitored using artificial intelligence (AI) and remote sensing technologies. FIG. 14 is an illustration of monitoring breathing rate using remote sensing technology. Changes in breathing rate or characteristic breathing rate histograms may indicate the existence of a medical emergency. Another example is collecting data using different sensors during sleep in bed, like sweeting, heart rate, respiration, body temperature, sleeping cycle (REM (rapid eyes movement) sleep, NREM (non-rapid eyes movement) sleep, deep sleep, light sleep, etc.), breath rate, blood pressure. It should be understood that any sensor that is capable of collecting body characteristic data can be used in the method and system of the present disclosure. For example, radar systems may be configured to sense respiration and heart rates, in addition to or instead of movement and position information. In another example, sensed data and data histories may be combined to determine whether a medical emergency is indicated. For example, body and location position information may indicate a monitored person is taking a bath. In such a circumstance, a temperature inconsistent with taking a bath, a duration longer than an expected duration, etc., may generate a danger situation. In another example, a person who normally takes a three hour nap in the afternoon on the couch might trigger an alert when sensed data indicates a nap is lasting a threshold period of time longer than a typical nap, when the sensed data indicates an unexpected temperature or temperature change, etc. An "alert" status will be sent out when it is determined a person is in a "danger" situation. As illustrated, the system 400 has a sensing device 402 which may be attached to the person and configured to sense one or more indications of a person's health, such as one or more vital signs. As illustrated, the sensing device 402 sends out a signal to one or more detectors 404, for example, periodically. The detectors 404 receive the signals from the sensor 402 and forward the signals to a transceiver 406 which is communicatively coupled to a central processing system 408. The central processing system 408 has one or more processors P, one or more memories 410 and one or more data bases 412, and may be configured to process the signals to determine an indication of the person's health status at various time periods and based on signals received regarding the person's health, such as indicators of a person's heart/breathing rate, blood oxygen, temperature, blood pressure, blood sugar levels, etc. This determination may be used to determine whether there is an indication the person needs assistance. The determinations may be based on other criteria and data, such as information and criteria discussed above with respect to FIG. 1, active requests for assistance (e.g., pressing a help button on a pendant or mobile phone, calling a number, making a gesture indicative of a request for help, verbally requesting assistance), incomplete attempts to request assistance (e.g., reaching for a phone, partially completing a gesture indicative of a request for assistance). Other sensors, such as location sensors, may be employed in some embodiments. The system 400 may employ an artificial intelligence (AI) processing module 414 to analyze received data and stored records to determine whether an alert status should be indicated. The system 400 has a configuration interface 416 configured to provide configuration information to the system 400.

Figure 5:
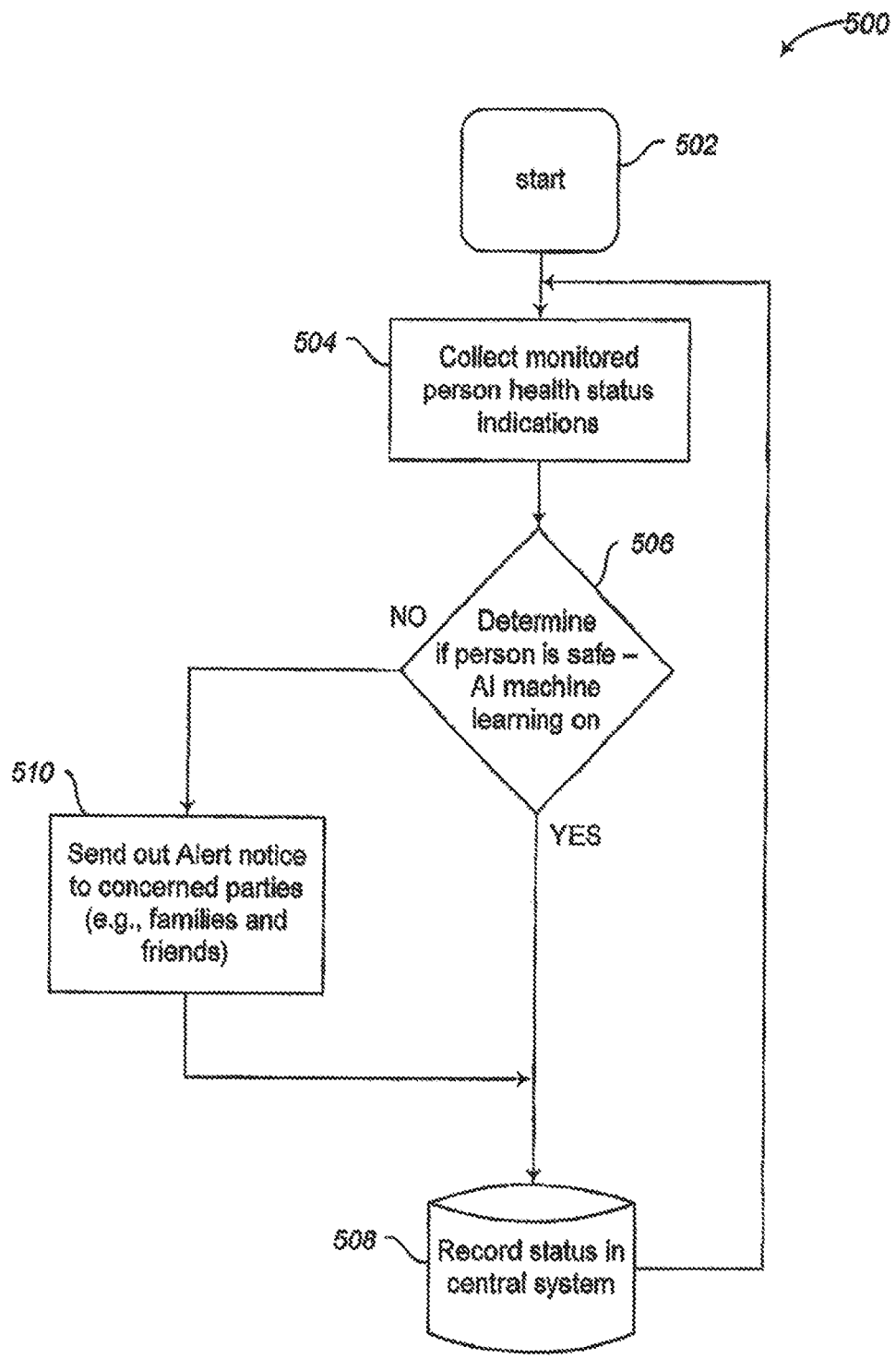
FIG. 5 is a flow diagram of a method of monitoring a health condition of a person.

FIG. 5 is a flow diagram of an embodiment of a method 500 of monitoring indications of a person's health status, for example to determine whether there is an indication the person may need assistance based on information related to the person's health status. As illustrated, the method 500 determines whether there is an indication the person is safe or unsafe. The method 500 starts at block 502 and proceeds to block 504. At block 504, the method 500 gathers health related information and proceeds at block 506 to determine based on the gathered information whether there is an indication the person needs assistance. The determination may be based on the absence of information, the change or lack of change of the information, other information (for example, location information, information about the person's physical orientation, time of day), etc. When it is not determined that there is an indication the person needs assistance (as illustrated, when it is determined the person is safe), the method 500 proceeds to update status information in a database at block 508, for example, to indicate that at a particular time the person is in a particular location and has a particular physical orientation.

When it is determined at block 506 that there is an indication the person may need assistance (as illustrated, a determination the person is unsafe), the method 500 proceeds to generate and transmit alert notices to concerned parties (e.g., family and friends via designated devices) and/or to take other actions as appropriate (e.g., turn on lights, turn off a stove, turn off water, lock or unlock a door, open or close a door or window, etc). The method 500 then proceeds to block 508 to update status information, as discussed above. The method 500 proceeds from block 508 to block 504.

The embodiment of the system 100 of FIG. 1, the embodiment of the system 200 of FIG. 2, and the embodiment of the system 400 of FIG. 4, may be configured to perform all or part of the method 500. Other systems (e.g., the system 600 of FIG. 6), and various combinations of systems or components thereof may be employed to implement all or part of the method 500 of FIG. 5.

Figure 6:
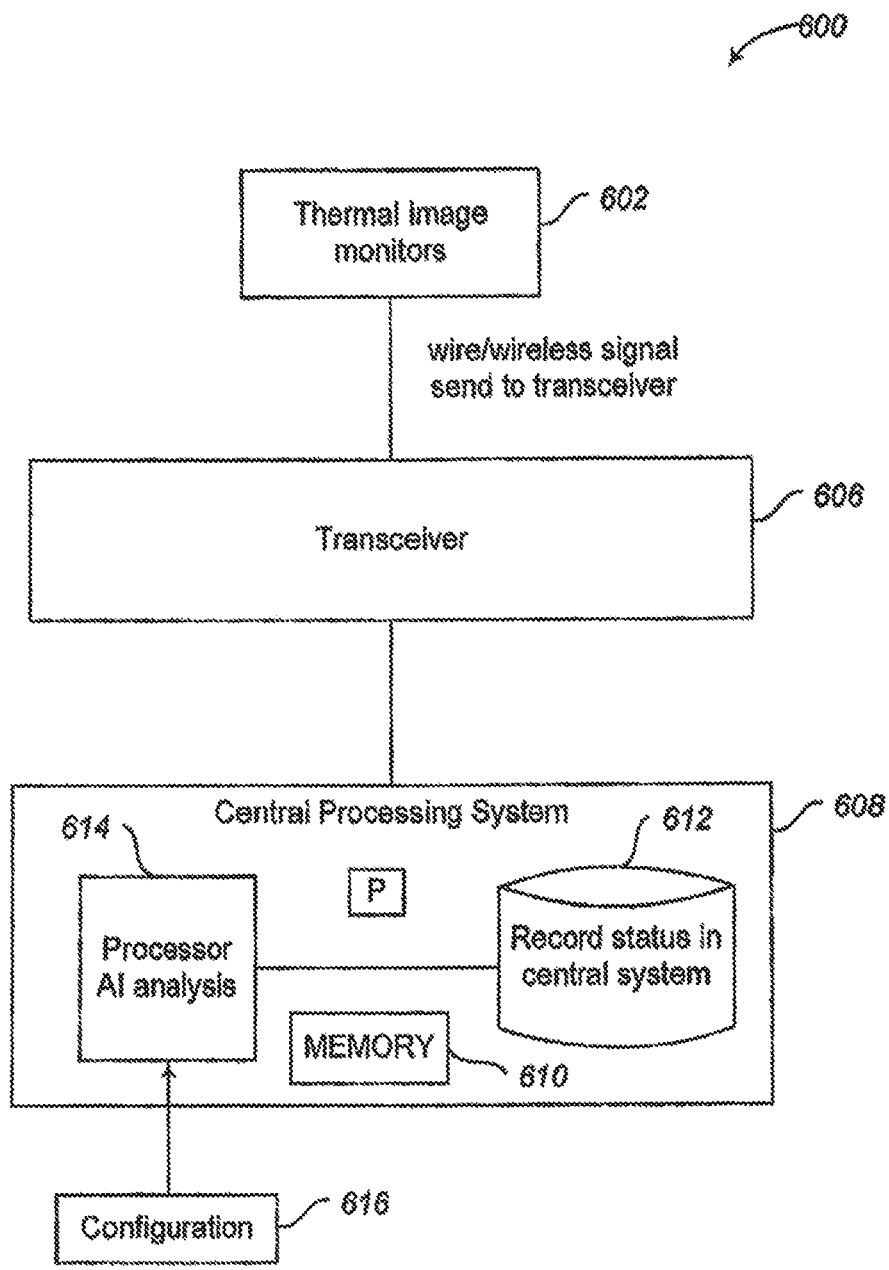
FIG. 6 is a functional block diagram of an embodiment of an environment suitable for providing monitoring and tracking services.

FIG. 6 shows an embodiment of a system 600 configured to monitor whether a person needs assistance based on thermal imaging. In an embodiment, a thermal image monitoring system 600 employs one or more infrared sensors 602. For example, a number of strategically placed thermal cameras may be installed on a property. Recorded status may be sent to the central processing system database 612, and any status changes may be recorded with time stamps. In an embodiment no personal identification may be stored in this system, ensuring that the privacy of the person will be protected. An "alert" status will be sent out when it is determined there is an indication the person is in a "danger" situation. For example, it may be determined whether there is an indication the person is in danger using various analysis systems immediately after images have been recorded as follows:

i) An AI image recognition system 614 may be configured to analyze and determine the status of the human "object" (sitting, standing, reading, fighting, fallen, crawling on the floor, not moving, etc.). An alert status may be sent when the algorithms detect that the person could be in a "danger" situation.

ii) A human monitoring analysis person (e.g., a doctor, nurse) or group (e.g., nurses, nurse aides) may monitor the images, and members may note any changes in the status of the images. The group may also determine whether the conditions constitute a "danger" situation, in which case an alert may be sent out. In an embodiment, permission may be required for human monitoring. In some embodiments, data in addition to or instead of images may be made available for remote monitoring. Such approaches may be less invasive that summing assistance to the monitored individual's residence.

iii) A combined approach, for example, an automated system that sends alerts to a human monitoring analysis group. For example, the monitoring system may also be configured to flag particular images or image sequences for review by the monitoring analysis group.

As illustrated, the thermal sensing device(s) 602 send out a signal to one or more transceivers 606, for example, periodically. The transceiver 606 is communicatively coupled to a central processing system 608. The central processing system has one or more processors P, one or more memories 610 and one or more data bases 612, and may be configured to process the signals to determine an indication of the person's orientation at various time periods and based on signals or images received related to the person's orientation (e.g., sitting, standing, reading, fighting, sleeping, crawling, bathing, etc.). This determination may be used to determine whether there is an indication the person needs assistance. The determinations may be based on other criteria and data, such as information and criteria discussed above with respect to FIG. 1. Other sensors, such as location sensors, health status sensors, other orientation sensors, may be employed in some embodiments. It is noted that the thermal image sensors may provide location sensing and health status information (such as temperature and breathing rates, etc.) without being physically coupled to the person whose status is being monitored. The system 600 comprises a configuration interface 616 (e.g., a keyboard, a Bluetooth receiver, etc.) to facilitate configuration of the system 600. Distributed systems may be employed (e.g., web-based AI servers).

Figure 7:
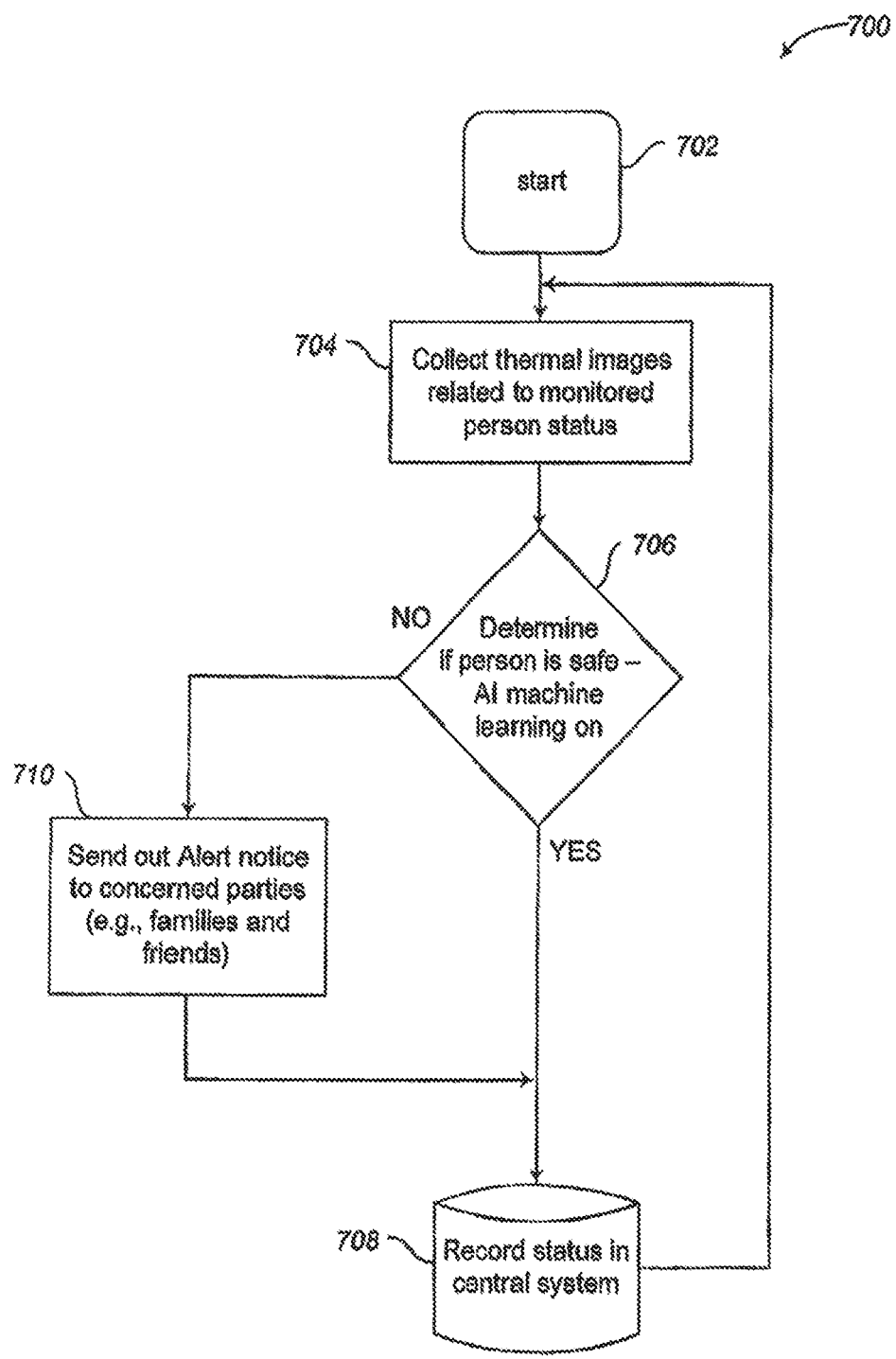
FIG. 7 is a flow diagram of a method of monitoring a person based on thermal images.

FIG. 7 is a flow diagram of an embodiment of a method 700 of monitoring indications of a person's safety based on thermal images, for example to determine whether there is an indication the person may need assistance based on information related to the person's location, physical orientation, health status, etc. As illustrated, the method 700 determines whether there is an indication the person is safe. The method starts at block 702 and proceeds to block 704 to gather thermal images and extracts information therefrom and proceeds to determine at block 706 based on the gathered images and extracted information whether there is an indication the person needs assistance. The determination may be based on the absence of information, the change or lack of change of the information, other information (for example, other location information, other health-status information, time of day), etc. When it is not determined that there is an indication the person needs assistance (as illustrated, when it is determined the person is safe), the method 700 proceeds to block 708 to update status information in a database, for example, to indicate that at a particular time the person is in a particular location, has a particular orientation, etc.

When it is determined at block 706 that there is an indication the person may need assistance (as illustrated, a determination the person is unsafe), the method 700 proceeds at block 710 to generate and transmit alert notices to concerned parties (e.g., family and friends via designated devices) and/or to take other action as appropriate (e.g., asking the person if they are alright before triggering an alarm). The method 700 then proceeds to block 708 update status information, as discussed above. The method 700 proceeds from block 708 to block 704.

The embodiment of the system 600 of FIG. 6, the embodiment of the system 200 of FIG. 2, and the embodiment of the system 400 of FIG. 4 may be configured to perform all or part of the method 700. Other systems (e.g., the system 100 of FIG. 1, etc.), and various combinations of systems or components thereof may be employed to implement all or part of the method 700 of FIG. 7.

Figure 8:
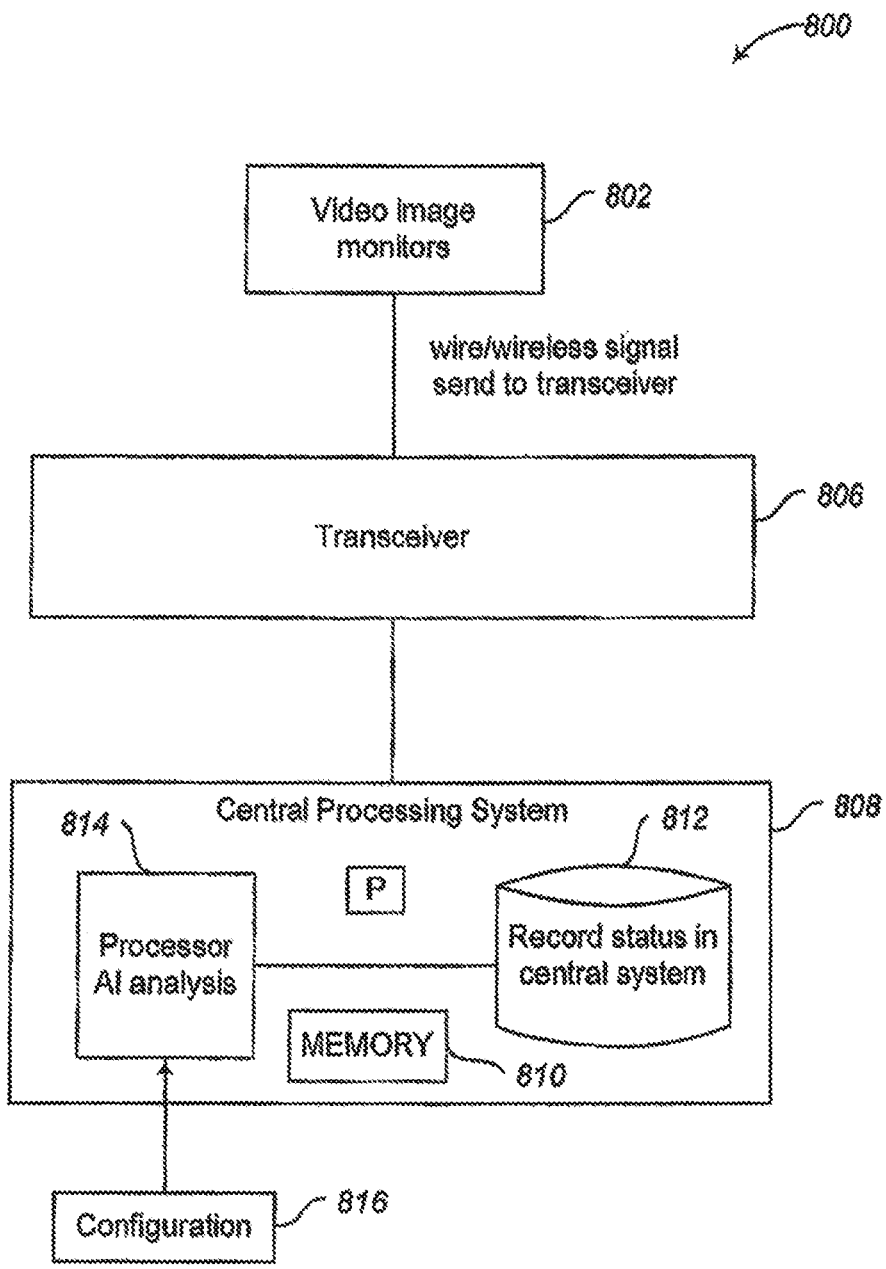
FIG. 8 is a functional block diagram of an embodiment of an environment suitable for providing monitoring and tracking services.

FIG. 8 shows an embodiment of a system 800 configured to monitor whether a person needs assistance based on video imaging. In an embodiment, a video image monitoring system 800 employs one or more video cameras 802. For example, a number of strategically placed video cameras may be installed on a property. Recorded status may be sent to a central processing system database 812, and any status changes may be recorded with time stamps. An "alert" status may be sent out when it is determined there is an indication the person is in a "danger" situation. For example, it may be determined whether there is an indication the person is in danger using various analysis systems immediately after images have been recorded as follows:

i) An AI image recognition system 814 configured to analyze and determine the status of the human "object" (sitting, standing, reading, fighting, fallen, crawling on the floor, etc.). An alert status may be sent when algorithms of the AI system 814 detect that the person could be in a "danger" situation.

ii) A human monitoring analysis group (e.g., nurses) may monitor the images, and members of the group may note any changes in the images. The group may also determine whether the conditions constitute a "danger" situation, in which case an alert may be sent out.

iii) A combined approach, for example, an automated system that sends alerts to a human monitoring analysis group. This might be desirable to reduce false positive alerts or to lower the threshold for an automatic alert, etc. The automated system may store responses determined by the group and employ the information to update the algorithms (e.g., to reduce false triggers by the automated system).

As illustrated, the video recording device(s) 802 send out video signals to one or more transceivers 806, for example, periodically. The transceiver 806 is communicatively coupled to a central processing system 808. The central processing system has one or more processors P, one or more memories 810 and one or more data bases 812, and may be configured to process the signals to determine an indication of the person's orientation at various time periods and based on signals received regarding the person's orientation (e.g., sitting, standing, reading, fighting, sleeping, crawling, bathing, etc.). This determination may be used to determine whether there is an indication the person needs assistance. The determinations may be based on other criteria and data, such as information and criteria discussed above with respect to FIG. 1. Other sensors, such as location sensors, health status sensors, thermal sensors, and various combinations, may be employed in some embodiments. It is noted that the video image sensors 802 may provide location sensing and health status information (such as breathing rates, etc.) without being physically coupled to the person whose status is being monitored. The system 800 comprises a configuration interface 816 (e.g., a keyboard, a Bluetooth receiver, etc.) to facilitate configuration of the system 800.

Figure 9:
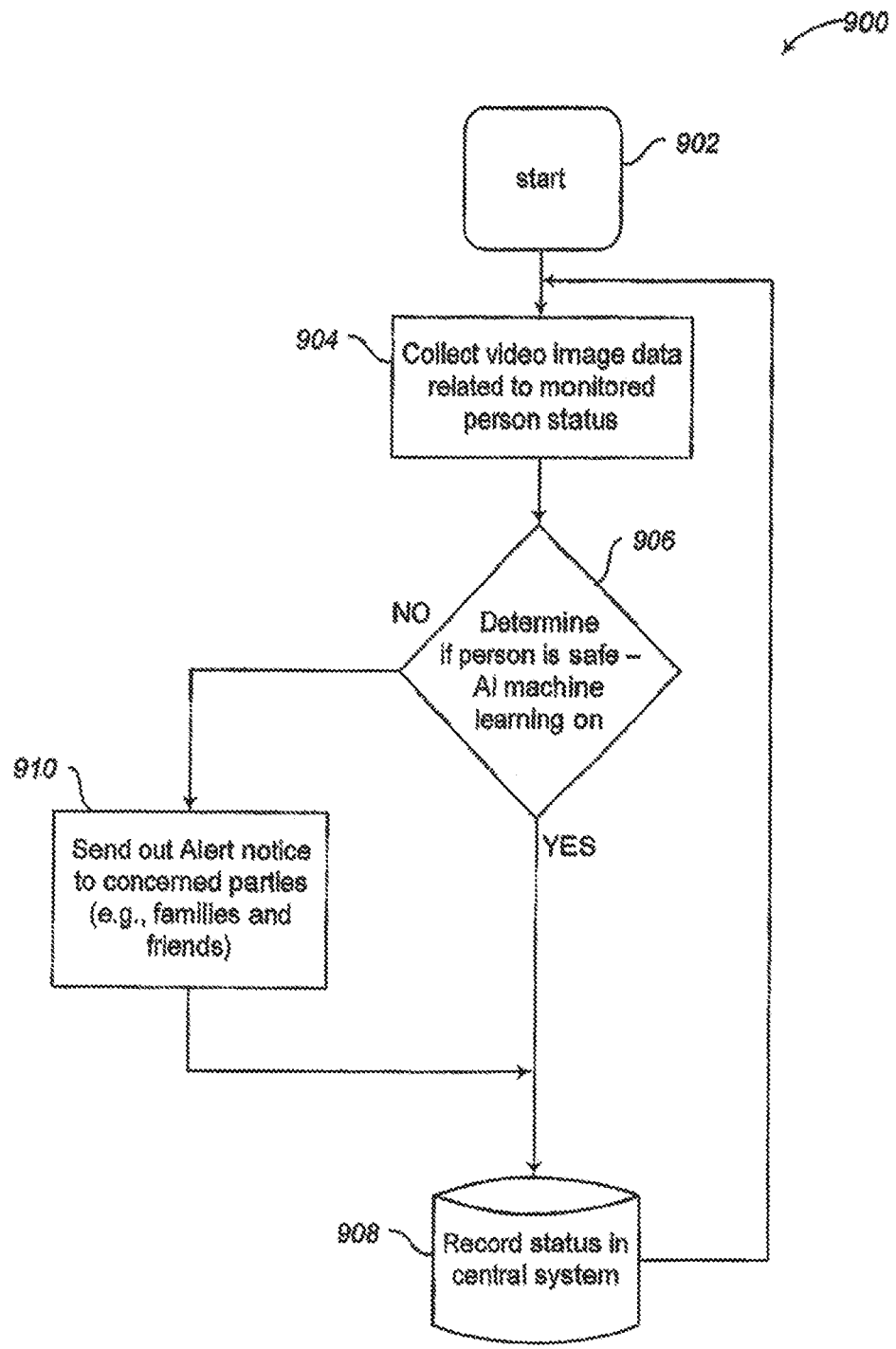
FIG. 9 is a flow diagram of a method of monitoring a person based on video images.

FIG. 9 is a flow diagram of an embodiment of a method 900 of monitoring indications of a person's safety based on video images, for example to determine whether there is an indication the person may need assistance based on information related to the person's location, physical orientation, health status, etc. As illustrated, the method 900 determines whether there is an indication the person is safe. The method starts at block 902 and proceeds to block 904 to gather video images and extract information therefrom and proceeds to block 906 to determine based on the gathered images and extracted information whether there is an indication the person needs assistance. The determination may be based on the absence of information, the change or lack of change of the information, other information (for example, other location information, other health-status information, time of day), etc. When it is not determined at block 906 that there is an indication the person needs assistance (as illustrated, when it is determined the person is safe), the method 900 proceeds to block 908 to update status information in a database, for example, to indicate that at a particular time the person is in a particular location, has a particular breathing rate, temperature, etc.

When it is determined at block 906 that there is an indication the person may need assistance (as illustrated, a determination the person is not safe), the method 900 proceeds to block 910 to generate and transmit alert notices to concerned parties (e.g., family and friends via designated devices) and/or to take other action as appropriate (e.g., to request data from one or more sensor related to a condition suggesting the person might need assistance, etc.). The method 900 then proceeds to update status information at block 908, as discussed above. The method 900 proceeds from block 908 to block 904.

The embodiment of the system 800 of FIG. 8, the embodiment of the system 200 of FIG. 2, and the embodiment of the system 400 of FIG. 4 may be configured to perform all or part of the method 700. Other systems (e.g., the system 600 of FIG. 6, etc.), and various combinations of systems or components thereof may be employed to implement all or part of the method 900 of FIG. 9.

Embodiments of methods described or illustrated herein may contain additional acts not described or shown in the figures, may not contain all of the acts described or shown in the figures, may perform acts described or shown in various orders, and may be modified in various respects. For example, the determinations illustrated in FIGS. 1, 3, 5, 7 and 9 may in some embodiments be made based on a combination of the various types of data gathered by the systems illustrated in FIGS. 1, 2, 4, 6 and 8. For example, a monitoring system may employ a combination of location sensors coupled to a person, health sensors coupled to a person, thermal sensors, video sensors, other sensors (such as window and door sensors), etc., to receive indications that may be employed to determine whether there is an indication that a person needs assistance. In another example, the process may be iterative. For example, one or more of the described methods may respond to an indication that a person may be in danger by gathering additional information before determining to generate an alarm signal.

Figure 10:
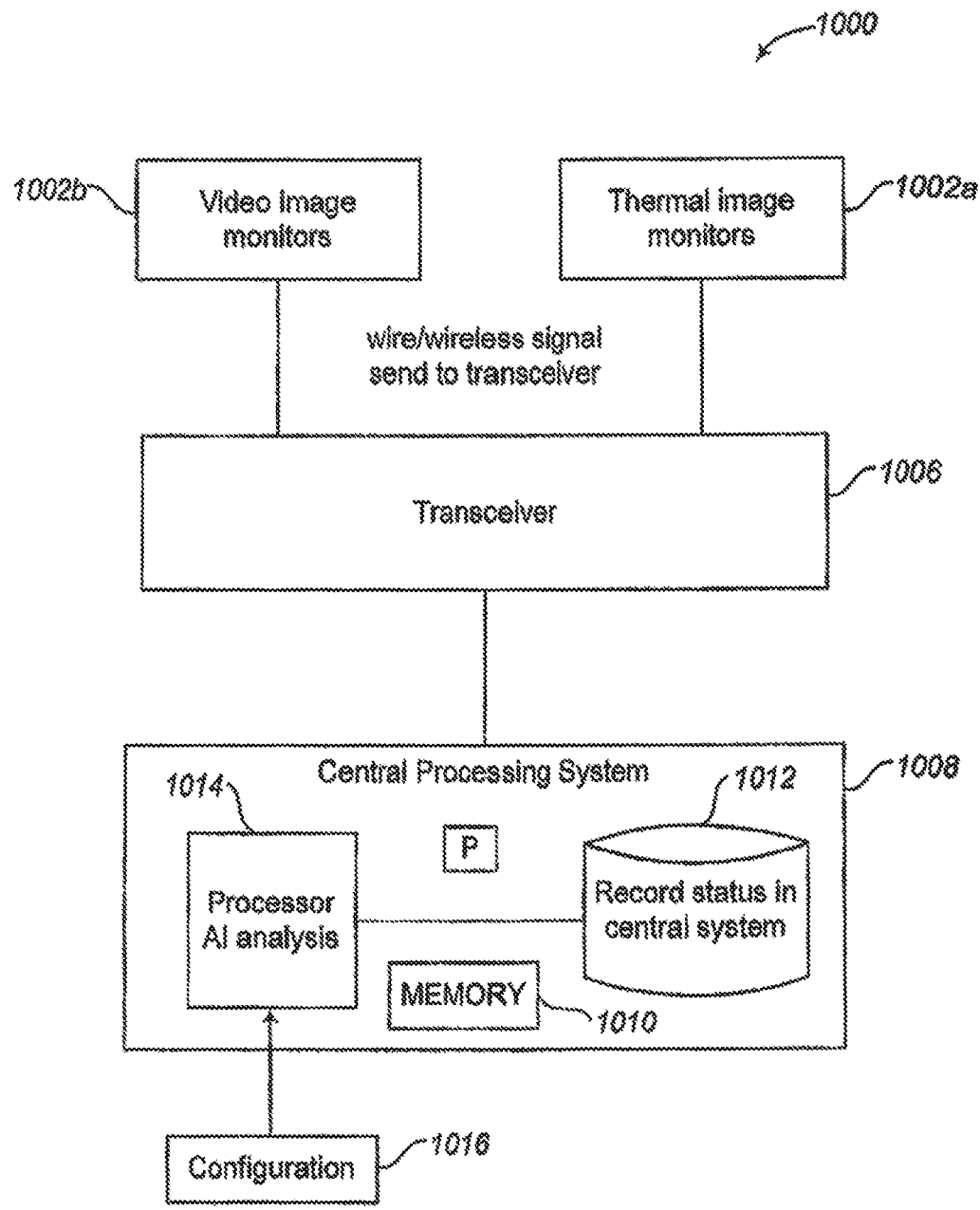
FIG. 10 is a functional block diagram of an embodiment of an environment suitable for providing monitoring and tracking services.

For example, FIG. 10 illustrates an embodiment of a monitoring system 1000 employing both thermal image sensors 1002a and video image monitors 1002b. Such an embodiment may be employed, for example, when it is desirable to monitor places such as bathrooms, where thermal sensors might be employed to increase privacy, as well as more public places, such as living rooms and outside decks. Data from thermal sensors and video image monitors may be combined in some embodiments.

As illustrated, the monitors 1002a, 1002b send out signals to one or more transceivers 1006, for example, periodically. The transceiver 1006 is communicatively coupled to a central processing system 1008. The central processing system has one or more processors P, one or more memories 1010 and one or more data bases 1012, and may be configured to process the signals to determine an indication of the person's conditions at various time periods and based on signals received regarding the person's conditions (e.g., orientation conditions (sitting, standing, reading, fighting, sleeping, crawling, bathing, etc.); health status conditions, facial expressions, etc.). These determinations may be used to determine whether there is an indication the person needs assistance. The determinations may be based on other criteria and data, such as information and criteria discussed above with respect to FIG. 1. Other sensors, such as location sensors, health status sensors, thermal sensors, and various combinations, may be employed in some embodiments. The system 1000 comprises a configuration interface 1016 (e.g., a keyboard, a Bluetooth receiver, etc.) to facilitate configuration of the system 1000. Detectors (see detector 104 of FIG. 1) may be employed in some embodiments.

At least some embodiments of a monitoring system may have full duplex communication ability where a monitored person (MP) can communicate with a) the computer system; and b) people who locate in a data communication center (e.g., an ONSTAR® communication center), and vice versa.

In an embodiment, the monitoring system includes AI machine learning algorithms (implemented, for example, by AI modules such as the AI module 114 of FIG. 1) that may increasingly identify objects, human physical movement and their facial expressions to determine and/or verify whether the study subject (human) is at risk. The monitoring system may be configured to predict events by recognizing patterns of movement or behaviors that typically precede them. For example, before collapsing, many people will sway back and forth or side to side. Similarly, repeating walking patterns over and over could signal confusion induced by some medical condition. On the other hand, for some people repeating walking patterns (e.g., pacing in a particular place) may be a normal occurrence.

In an embodiment, a threshold for triggering a "danger" red flag has 3 levels which are based on statistical analysis of the data collection from the normal behavior of the study human (MP). If a movement, living habit, facial expression or any other abnormal behavior appears (which may fall off a pre-set threshold percentile in the normal distribution range of a bell curve—e.g. 68%—one standard deviation from the mean), an alarm may be triggered and this statistical analysis may be captured to be used in the future to improve accuracy as part of the AI machine learning process.

AI and other data analysis may be employed which relies on one or more of global predictions (e.g., predictions based on histograms associated with a generic population), demographic based predictions (e.g., predictions based on histograms associated with a specific demographic (e.g., the population of a particular city or region, people of a particular race or age or other risk factor, combinations thereof)), and individual based predictions (e.g., predictions based on histograms associated with a specific individual (e.g., a person's history of movement), and various combinations thereof.

In an embodiment, a monitoring computer system may also accomplish normal daily tasks with voice commands to control household electronic devices like:

Setting an alarm clock,

Reminders for daily activities like taking pills, cooking times, setting calendar event reminders, etc.

Making phone calls using the full duplex system simply by asking: "Amina (referring to an example brand name for a monitoring system), please call my son" (or some similar phrase to activate a phone call).

Turn on/off and make adjustment to household devices (e.g. TV, radio control, audio devices, volume control, channel switching, open/close or adjust the blinds/curtains, etc.)

In an embodiment, the voice commands may be used to trigger an alert. In an embodiment, the system may prompt a user to respond. No response, an inappropriate response, or a response which does not correspond to an expected response may prompt an alert. In an embodiment, voice recognition subsystems may be employed, for example, to identify voice commands, to authenticate voice commands, to identify the person to be monitored (e.g. to trigger a robot to move to better monitor the person), to identify another person in a monitored location, etc., and various combinations thereof. In an embodiment, a push to talk system may be employed.

In an embodiment, a monitoring system may also be a secure alarm system which can detect any invader/thief entering the property without permission. AI algorithms may be employed to reduce false alarms for the monitoring system as well (e.g., time information, human recognition information, pattern recognition, etc.)

In an embodiment, the components of a monitoring system (e.g., the systems of FIGS. 1, 4, 6 and 8) might include Image capture devices (infrared, 3-D camera).

An embodiment might include AI machine learning systems (e.g., AI systems 114, 414, 614 and 814 of FIGS. 1, 4, 6 and 8) where algorithms in the system are configured to analyze and define a monitored person's properties and a monitored person's environment properties, identify whether the monitored person is at risk, for example by using AI system identifiers as discussed below. The AI identifiers might comprise, for example, Object identifiers (which define human, animal, and other objects—chair, table, sofa, etc.); Location identifiers (which define a monitored persons location—bedroom, bathroom, kitchen, etc.); Position identifiers (which define a position such as sitting, lying down, crawling, etc.); Time identifiers (which identify the time of the day when a monitored person is in each location); Sound identifiers (which identify sounds generated by human and non-human objects—e.g. Microwave, fire alarm, TV, etc.); Motion identifiers (which identify body movement characteristics); Physical Status identifier (which identify physical health condition characteristics); Emotional identifiers (which, for example, identify facial expression characteristics, other physical characteristics indicative of emotion (e.g., position, temperature, smells, etc.)); Motion and Emotional identifiers (which, for example, identify both facial expression and body movement characteristics); etc., and various combinations thereof.

At least some embodiments are configured to communicate with a remote communication call center, which can directly communicate to the monitored person's household with a full duplex communication (two-way) ability.

At least some embodiments may comprise a secure network system where digital information (e.g. data record, images, etc.) can be transmitted to the computer servers, CPU, emergency communication center and any nodes/parties within the network. A secure full duplex voice communication can be transmitted to different nodes/parties within the network.

At least some embodiments may be configured to provide reports and/or access to other devices (e.g. handheld devices, computers, etc.) where authorized interested parties (e.g. a monitored person's families and friends) may access the recorded record of the MP proprieties (e.g. record of how long the MP slept last night; what is the average nap time in the afternoon, etc.).

In at least some embodiments, an AI system of a monitoring system (e.g., AI systems 114, 414, 614, 814, 1014 of systems 100, 400, 600, 800, 1000 of FIGS. 1, 4, 6, 8 and 10) may use one or more of the following identifiers to identify different properties of a monitored person and a monitored person's environment: Object identifiers (define human, animal, or other object—chair, table, etc.); Location identifiers (define the MP's location—bedroom, bathroom, kitchen, etc.) Position identifiers (sitting, lying down, crawling, etc.); Time identifiers (identify the time of the day when the MP is in each location); Sound identifiers (Sound that is generated by human and non-human objects—e.g. Microwave, fire alarm, TV, etc); Motion identifiers (body movement characteristics); Emotional identifier (facial expression characteristics); Physical status identifier (which identify health condition characteristics—e.g. heart rate, blood glucose content, cold sweat, etc); Motion and Emotional identifier (both facial expression and body movement characteristics); etc.; and various combinations thereof.

Monitored person properties that are defined by the above identifiers may be used to generate different measurements to compare to a threshold to trigger an alarm. This collection of data is not limited to, but includes the following properties: locations; pattern of facial movement; pattern of body movement; hours of the day and night in different locations of the monitoring property; pattern of voice, tone, and any sound related properties; physical body condition; the combination of two or more of the above properties; etc. An AI system accuracy may increase with the AI machine learning algorithms by collecting more observation data (characteristics/properties collection is defined by different identifiers—see above identifier's definition). With the continuously increasing the data set, the accuracy may increase every day with the AI ability of learning.

The collection data that improves the AI machine learning algorithms may include: (1) a current monitored person's properties (e.g. body movement and facial activities); and (2) other studied human subject's properties that are collected outside the current monitored person.

In an embodiment, different alarm levels and responses thereto may be employed. For example, a Level 1 alarm condition may cause a monitoring system (e.g., system 100 of FIG. 1) to call a monitored person using a full duplex voice communication system when an abnormal behavior/characteristic is detected. If the monitored person responds, "it's fine", the system may learn this as new pattern property to increase future recognition accuracy. If there is no response from the MP, a "level 2" alarm may be triggered. In an embodiment, a Level 2 alarm may send signals to a monitoring data center (e.g., monitoring center 120 of FIG. 1) indicating real people at the monitoring data center should call the monitored person. In an embodiment, if the monitored person does not answer, a Level 3 alarm may be triggered. In an embodiment, a Level 3 alarm may indicate the data center should follow emergency steps to contact relatives/friends, fire fighters, medics, hospital/health care providers, etc. The monitored person/family member(s) may provide this emergency list of contacts when signing up for this monitoring system or configuring the monitoring system. In some embodiment, the Levels may trigger different responses, and additional levels may be employed. For example, the monitoring system may send an automated message based on emergency contact information before contacting a remote communication center under specified conditions.

The stages of the alarm level may be recorded and the AI machine learning configured to learn when false alarms are being triggered. This new pattern of abnormal properties/behaviors/characteristics which triggered the alarm may be stored and thus learned. The system may use the stored patterns to improve the accuracy of predictions in the future as part of the AI machine learning process.

Figure 11:
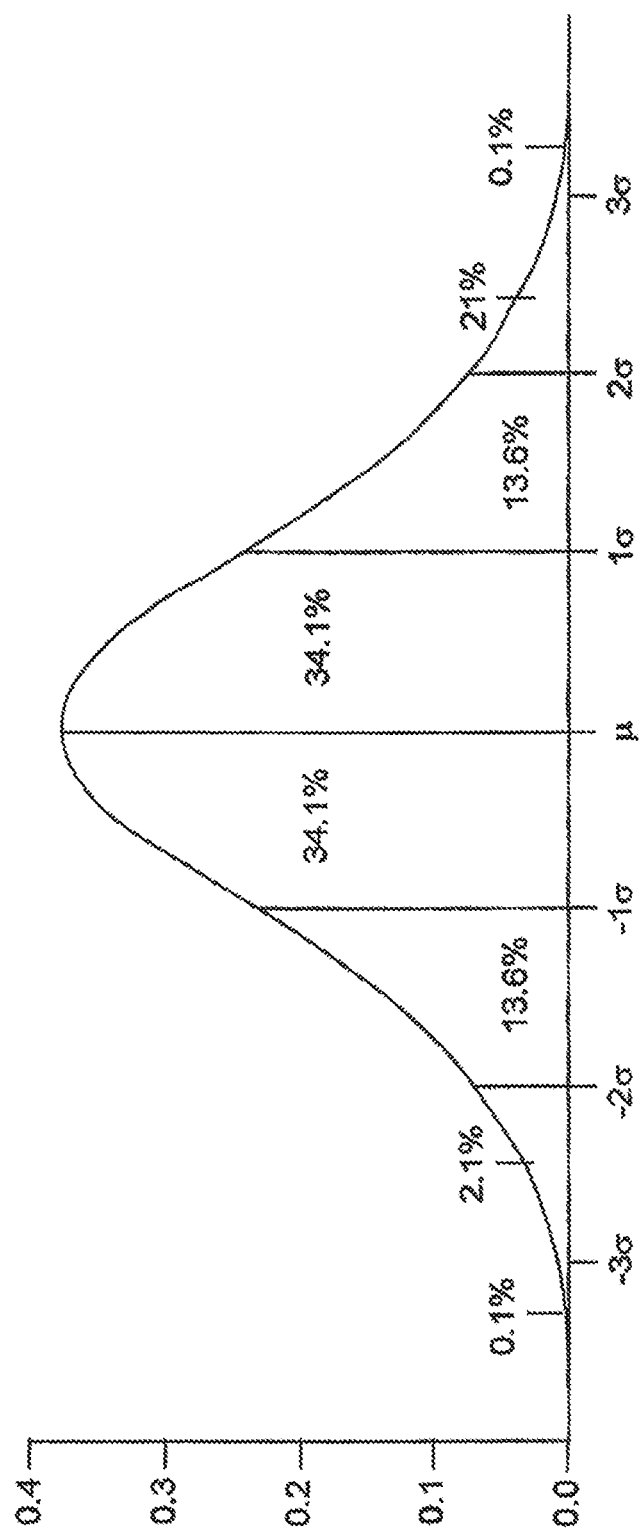
FIG. 11 is an illustration of an example property-identifier curve.

In an embodiment, a prediction may be based on previously studied statistic analysis of patterns in properties (e.g. movement, facial expression), and predict and define normal characteristics (e.g. facial expression, body movement, hours of sleep, location of sleep—nap in sofa during daytime vs. bedroom sleep at night). If the prediction falls beyond a threshold (e.g., a standard threshold such as 68.2% (34.1%+34.2%) line—the threshold number may be edited according to the situation and the consensus between the MP/MP's family and the programmer) from a normal distribution curve, an alarm will be triggered. FIG. 11 shows an example of thresholds employed in a Bell curve.

In an embodiment, an AI algorithm is configured to predict movement of a monitored person based on: (1) the current MP's properties (e.g. body movement and facial activities); and (2) other studied human subject's properties that are collected outside the current MP. When the recorded priorities fall beyond a threshold percentile (e.g., 68%—one standard deviation from the mean) of the predicted properties (e.g., movement sequence; staying in the bathroom longer than the standard threshold), an alarm may be triggered. In an embodiment, a threshold curve of properties measurement may change accordingly as the AI system continues to learn, develop and improve the accuracy with the AI machine learning ability. The AI system will learn, justify/adjust threshold(s), and tailor responses toward the living habits of an individual monitored person.

For example, if a Tai Chi series pattern of movements has never been observed and recorded, the alarm may be triggered as the MP's properties are beyond the normal threshold percentile. However, as more and more recorded Tai Chi practice movement occurs, the system will learn and treat this series of Tai Chi moments as the MP's normal pattern of behavior. This also may be applied to facial movement, and other types of body movement and living behaviors (e.g., hours of sleep, left handed and right handed changes, body temperature changes, etc.).

In another example, an AI system may be configured to predict events by recognizing patterns of movement or behaviors that typically precede them—before collapsing, many people will sway back and forth or side to side, repeating walking patterns over and over could signal confusion induced by some medical condition, and there may be other characteristics that happen just before strokes or heart attacks.

In addition, each property (e.g. location; time) may have different thresholds of property percentile curve to trigger the alarm. The threshold of measurement may be different depending on a specific combination of identified properties.

In another example, the hours (time identifier) of laying down (position identifier) in the kitchen may be five minutes, laying down in the living room sofa (location identifier and object identifier) may be two hours, but the threshold of laying down in the bedroom may be six hours at night (12 am to 6 am) and three hours during daytime (1 pm to 6 pm). In other words, the location and time would have their own standard deviation threshold for any given time of the day and the location of the monitoring area.

In another example, a monitored person may normally stay in the bathroom for 30 minutes (e.g. +/−3% time different). If the monitored person stays longer in the bathroom more than this time frame, the alarm may be triggered.

In another example, a "Physical Status identifier" may identify physical health condition characteristics (e.g., a heart rate, blood glucose content, cold sweat condition, etc.). The physical characteristics may have their own pattern, or be including in the pattern comprising other characteristics, and a bell curve may be employed to determine a threshold by defining normal and abnormal body physical behavior based indicators related to those characteristics. I These types of property thresholds may also be edited according to the situation and the consensus between the MP (Monitored Person)/MP's family and the programmer (e.g. hours to sleep, where to sleep, etc.).

Embodiments may provide for flexible responses. For example, a monitoring person could choose the following when the alarm is being triggered: (1) send the full capture video to the call center or (2) choose not to send video to the call center. If a household has more than one monitored person that needs to monitored, the patterned and monitoring properties may be modified to fit the household condition. For example, it may be less focused on facial pattern and movement, but more focus on laying down properties in location, durations or location of stay in certain hours of the day (e.g. bathroom for less than 30 minutes during day time). In another example, the AI may employ identifiers to identify the monitored person (e.g., based on size, activity patterns, facial recognition, etc.) and be configured to consider these identifiers when determining whether a person is in danger and the appropriate response to such a determination.

Figure 12:
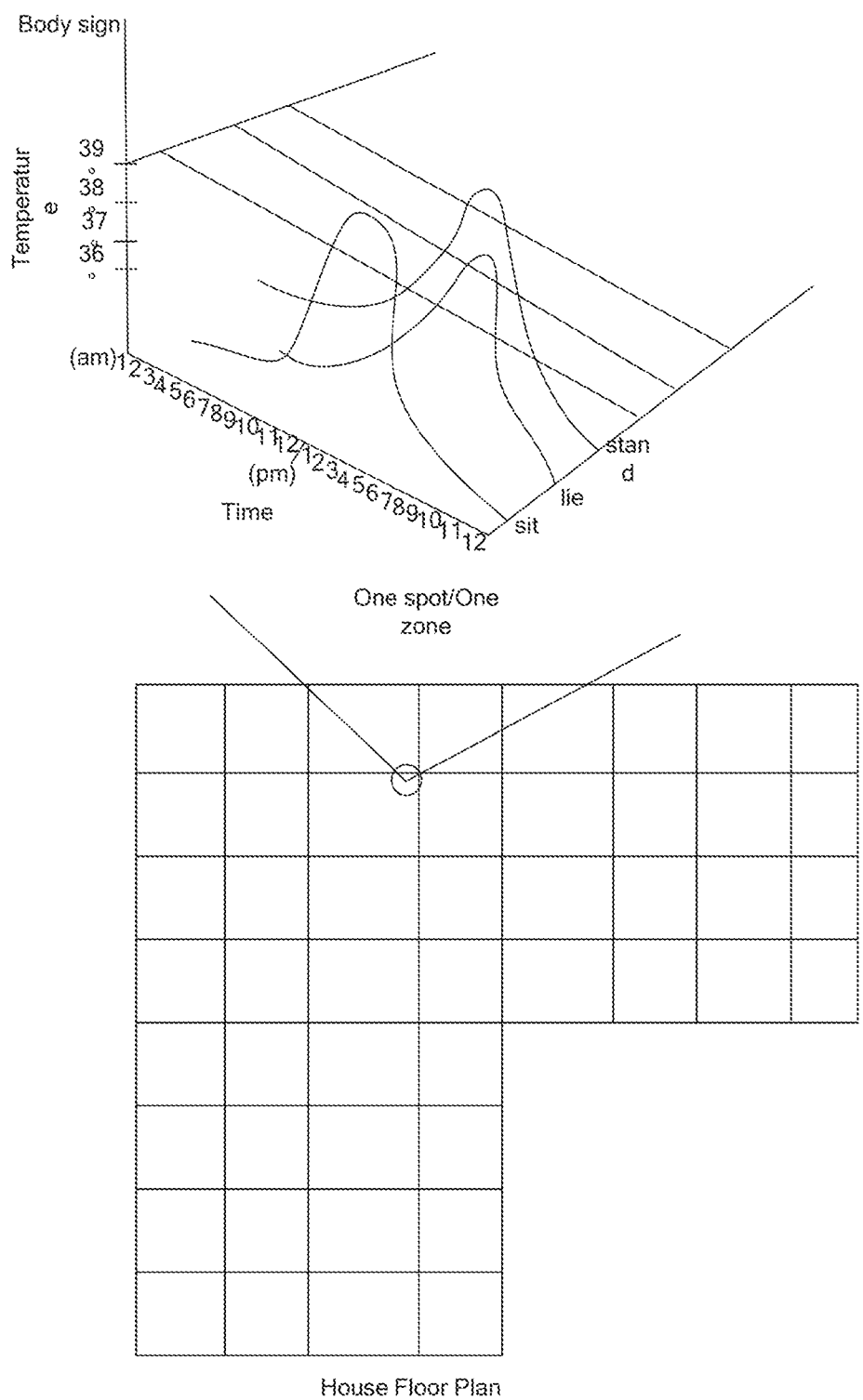
FIG. 12 illustrates example zone and spot based temperature curves.

In an embodiment, a robot with sensors (e.g., image, thermal, etc.) may follow an individual on a property instead of or in addition to using fixed sensors. An AI system using a statistical record pattern may employ spot and zone based pattern learning. FIG. 12 illustrates example zone and spot based temperature curves. In an embodiment, if a new behavior is detected (e.g., a behavior or condition inconsistent with past behavior which may indicated a person needs assistance), the system may prompt a monitored person (or a monitoring human) to confirm the behavior or condition does not indicate assistance is needed. If it is confirmed that the behavior or condition does not indicate assistance is needed, the system may update histogram data or other data to reflect that this type of behavior does not present a threat. If no response is received or a response is received indicating assistance is needed, the system may generate an alert. For example, a person may decide to employ a new exercise routine (e.g., yoga, aerobics, etc.) which the system may detect as a new behavior with associated data (e.g., movement periods, heart rates, temperatures, position information, etc). The system may prompt the monitored person or a monitoring person to confirm a dangerous situation is not presented. The system will learn that the new behavior does not present a danger (within certain parameters). In an embodiment, the robot or robots may perform other functions, e.g, vacuuming, playing music, controlling other appliances, connecting to the internet, placing phone calls, etc.). In an embodiment, a robot or other system component may be configured to respond to voice commands. In an embodiment, the robot may be able to provide assistance to the monitored person either in the normal course (e.g., carrying things for the person, assisting the person in getting up, pulling the person up, etc.), or in response to detection of a dangerous condition (e.g., assisting the person in getting up, pulling the person up, in addition to or instead of generating an alarm).

Global and zone or area based criteria may be employed. For example, monitoring in a work-out area and monitoring in a sleeping area may both employ global thresholds and histograms, while also using zone based thresholds and histograms. For example, the monitoring of the work-out area may also employ work-out area histograms and thresholds in addition to the global thresholds and conditions.

Various techniques and systems may be employed by the AI to interpret the sensor data and histograms. For example, artificial neural networks and various programs and systems (e.g., Tensile Flow, On Premise) may be employed. Sparse dictionaries and dictionary transforms may be employed. Support vector machines may be employed, etc., and various combinations thereof.

In some embodiments, various lenses may be employed, e.g., a wide angle 15 mm lens, a 70-90 degree fish eye, infrared lenses, etc.

In some embodiments, a monitored individual may be reminded to or prompted to perform certain activities. For example, if a monitored person has been sitting for a threshold period of time, the person may be prompted to walk, stand up or stretch. If a monitored person is supposed to take medicine and activity consistent with the taking of the medicine is not detected, the person may be prompted to take the medicine or to confirm the medicine has been taken, etc. The threshold may depend on the position of the person, the location of the person, the time of day, etc. For example, lying down in a bedroom for a certain number of hours may not generate a prompt or alert from the system if it is consistent with a normal sleeping pattern of the person. On the other hand, lying down in the kitchen may generate a prompt or alert after a few minutes or seconds. The time may depend on other factors (e.g., pulse, temperature, etc.).

Some embodiments may prompt a monitored person to eat or trigger an alarm if eating activity has not been detected for a threshold period of time. The threshold(s) may vary based on the response (e.g., a threshold for prompting may be shorter than a threshold for triggering an alert), global data (e.g., for most people), demographic data (e.g., diabetics), and specific data (e.g., the monitored person always eats at 9:00 a.m. on weekdays). Some embodiments may make predictions based on multiple factors, e.g., histogram data suggesting a low-blood sugar level, such as body temperature, position and the time since eating activity was observed.

Some embodiments may monitor a person for signs of depression (less body movement or different positions and times of body movement, failures to turn on lights consistent with prior behavior, etc.

Figure 13:
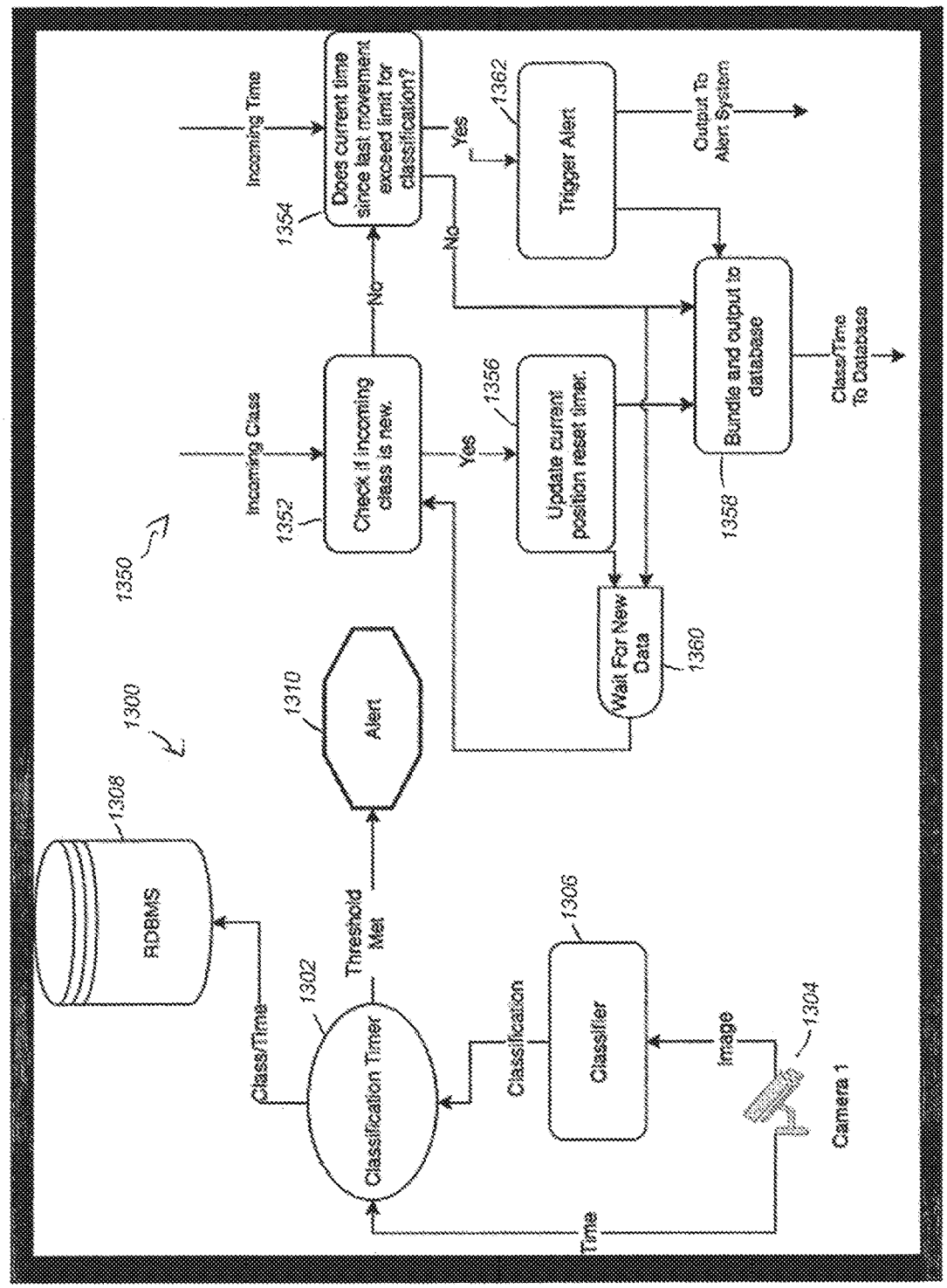
FIG. 13 illustrates an embodiment of a system and an embodiment of a method of operating a system, such as the various systems described herein, to monitor an individual.

FIG. 13 illustrate an embodiment of a system 1300 and a method 1350 of operating such a system. While method 1350 is described with reference to system 1300, other systems, such as the various other systems described herein, may be employed to monitor an individual and detect motion. In an embodiment, three images im0, im1 and im2 are captured and converted to a normalized grayscale. The pixels of the images are then passed through the function (img1-img0) and (img1-img2), and normalized again. The resulting image is a pixel-by-pixel map of motion during the capture time of the three images. In an embodiment, detection of a maximum time without movement may generate a value Y indicative of a time since movement occurred based on a classifier prediction. The classifier makes a prediction and reports the class, image name and time to a database. A program queries the data base to make certain the Y values do not exceed threshold Y values, which may be associated with the type of activity (e.g., sleeping, eating, watching TV, etc.). In an embodiment, the classifications are generated and passed to a motion detection and threshold analysis before being reported to a database (which may be remote, e.g., in a cloud). Local alerts are triggered. In an embodiment, both classification and trigger schemes may be employed (e.g., local evaluation followed by cloud evaluation, either of which may trigger a response (e.g., query to the monitored person, alert, etc.).

In FIG. 13, a system 1300 and a method 1350 are illustrated. Time information is provided to a classification timer 1302 and an image capture device 1304. The image capture device 1304, which as illustrated is a camera, captures images of an environment in which an individual is being monitored. The images are provided to classifier 1306, which classifies the images and provides the images to the classification timer 1302. The classification timer 1302 provides or retrieves class and time information (e.g., thresholds) associated with various dangerous conditions to/from a relational database management system 1308. Based on comparisons of the class and time information associated with images of an image stream to the information in the relational database system, an alert may be generated at 1310.

In method 1350, at 1352 the system 1300 checks whether an image of an image stream is associated with a new class, e.g., has the individual moved from a sitting position to a standing position. When it is not determined at 1352 that the image is associated with a new class, the method 1350 proceeds from 1352 to 1354, where it is determined whether the current time since the last movement is exceeded for the classification. When it is determined at 1352 that an image is associated with a new class, the method 1350 proceeds to 1356, where a current position timer is reset. The method 1350 proceeds from 1356 to 1358 and 1360.

When it is determined at 1354 that the current time since the last movement is exceeded for the classification, the method proceeds to 1362, where an alert trigger is generated. As illustrated, the alert trigger is provided to an alert system, and may contain information related to the classification and timing that triggered the alert trigger, which may be used by the alert system to determine an appropriate response. The method proceeds from 1362 to 1358.

When it is not determined at 1354 that the current time since the last movement is exceeded for the classification, the method proceeds to 1358 and 1360, where an alert trigger is generated. As illustrated, the alert trigger is provided to an alert system, and may contain information related to the classification and timing that triggered the alert trigger, which may be used by the alert system to determine an appropriate response. The method proceeds from 1362 to 1358.

At 1358, information related to the image of the image stream, such as timing and classification information, is provided to the relational database management system, which may use the data to train an AI system as discussed in more detail elsewhere herein. At 1360, the method 1350 waits for new data. When new data is received, the method proceeds from 1360 to 1352.

Embodiments of the method 1352 may perform acts in various orders, may combine acts, may divide acts into separate acts, may contain fewer or more acts than illustrated, may perform acts in parallel or in various orders, and various combinations thereof.

An embodiment may employ thermal data specific to regions of a monitored person, specific activities, etc. For example, the head of an individual may be identified (it is often the hottest part of a human) and data recorded and used to classify a situation as potentially hazardous. The table below shows an example database. As shown in the example, laying in the kitchen for 5 minutes with a temperature of 39 degrees C. triggers an alert.

| Time | Location | Position (posture) | Last move | Stay still | Body temperature (Celsius) |
| --- | --- | --- | --- | --- | --- |
| 13:57 | Living room | stand | 13:58 | 1 min | 37 |
| 14:05 | Kitchen | stand | 13:59 | 3 mins | 37 |
| 14:10 | Living room | sit | 14:06 | 4 mins | 38 |
| 14:20 | Kitchen | lay | 14:11 | 5 mins | 39 |

Some embodiments may monitor other environments and types of subjects, such as children in a school room or school yard, animals (e.g., dogs, pigs, cows, etc.) to identify abnormal behavior and/or dangerous situations (e.g., excessive heat, poor air quality), etc.

Figure 15:
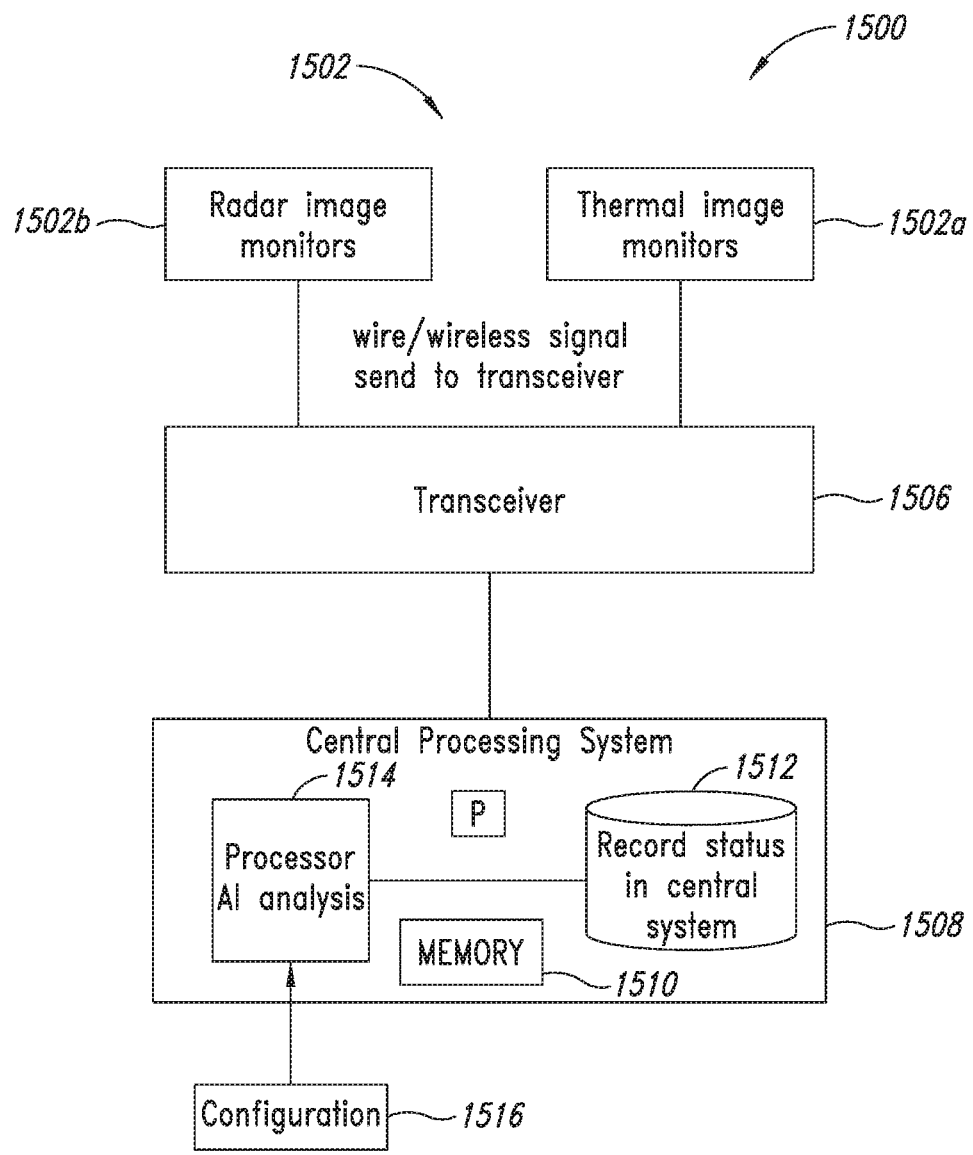
FIG. 15 is a functional block diagram of an embodiment of an environment suitable for providing monitoring and tracking services.

FIG. 15 illustrates an embodiment of a monitoring system 1500 employing a plurality of sensors 1502, as illustrated the plurality of sensors include thermal image sensors 1502a and radar images sensors 1502b. Such an embodiment may be employed, for example, when it is desirable to monitor places such as bathrooms, where thermal sensors or radar image sensors might be employed to increase privacy, as well as more public places, such as living rooms and outside decks. Data from thermal sensors, radar sensors and other sensors (e.g., lidar sensors, video image monitors, etc.) may be combined in some embodiments.

As illustrated, the sensors 1502a, 1502b send out signals to one or more transceivers 1506, for example, periodically. The transceiver 1506 is communicatively coupled to a central processing system 1508. The central processing system has one or more processors P, one or more memories 1510 and one or more data bases 1512, and may be configured to process the signals to determine an indication of the person's conditions at various time periods and based on signals received regarding the person's conditions (e.g., orientation conditions (sitting, standing, reading, fighting, sleeping, crawling, bathing, etc.); health status conditions; facial expressions; movement conditions (e.g., speed, direction, trajectory, potential and actually collisions, etc.); etc.)

These determinations may be used to determine whether there is an indication the person needs assistance. The determinations may be based on other criteria and data, such as information and criteria discussed above with respect to FIG. 1. Other sensors, such as location sensors, health status sensors, pendant sensors or devices, and various combinations, may be employed in some embodiments. The system 1500 comprises a configuration interface 1516 (e.g., a keyboard, a Bluetooth receiver, etc.) to facilitate configuration of the system 1500. Detectors (see detector 104 of FIG. 1) may be employed in some embodiments.

Some embodiments may take the form of or comprise computer program products. For example, according to one embodiment there is provided a computer readable medium comprising a computer program adapted to perform one or more of the methods or functions described above. The medium may be a physical storage medium such as for example a Read Only Memory (ROM) chip, or a disk such as a Digital Versatile Disk (DVD-ROM), Compact Disk (CD-ROM), a hard disk, a memory, a network, or a portable media article to be read by an appropriate drive or via an appropriate connection, including as encoded in one or more barcodes or other related codes stored on one or more such computer-readable mediums and being readable by an appropriate reader device.

Furthermore, in some embodiments, some or all of the methods and/or functionality may be implemented or provided in other manners, such as at least partially in firmware and/or hardware, including, but not limited to, one or more application-specific integrated circuits (ASICs), digital signal processors, discrete circuitry, logic gates, state machines, standard integrated circuits, controllers (e.g., by executing appropriate instructions, and including microcontrollers and/or embedded controllers), field-programmable gate arrays (FPGAs), complex programmable logic devices (CPLDs), etc., as well as devices that employ RFID technology, and various combinations thereof. For example, embodiments of a home monitoring system may be implemented as discussed above (e.g., partially in hardware, partially with controllers executing instructions, etc.).

The various embodiments described above can be combined to provide further embodiments. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A safety monitoring system, comprising:
 a plurality of sensors configured to generate signals indicative of a current condition related to a safety status of a person; and
 one or more processing devices coupled to the plurality of sensors and configured to:
  determine the safety status of the person based on the signals indicative of the current condition and stored information related to the safety status of the person;
  update the stored information related to the safety status of the person based on the signals indicative of the current condition; and
  in response to the determined safety status indicating the person may be in danger:
   initiate one or more actions based on the determined safety status;
   monitor responses to the one or more initiated actions; and
   update the stored information related to the safety status of the person based on the monitored responses.

2. The safety monitoring system of claim 1 wherein the one or more initiated actions comprise:
 generating an alert signal to the person;
 transmitting a signal to a remote server;
 generating an alert message based on stored contact information; or
 combinations thereof.

3. The safety monitoring system of claim 1 wherein the plurality of sensors include:
 a location sensor;
 a thermal sensor;
 a health status monitoring device;
 a radar sensor;
 a video capturing device; or
 combinations thereof.

4. The safety monitoring system of claim 1 comprising a device configured to perform voice communications.

5. The safety monitoring system of claim 1 wherein the stored information comprises property identifiers indicative of conditions and the one or more processing devices comprise an artificial intelligence module configured to compare the signals indicative of the current condition to the stored property identifiers and to determine the safety status of the person based on the comparison.

6. The safety monitoring system of claim 5 wherein the determining the safety status comprises determining a position of a property identifier on a characteristic property-identifier curve based on the signals indicative of the current condition.

7. The safety monitoring system of claim 6 wherein the characteristic property identifier curve is a Bell curve based on stored property identifiers indicative of the characteristic.

8. The safety monitoring system of claim 6 wherein the characteristic property-identifier curve is related to:
 an object identifier;
 a location identifier;
 a position identifier;
 a time identifier;
 a sound identifier;
 a motion identifier;
 a physical status identifier;
 an emotional identifier; or
 combinations thereof.

9. The safety monitoring system of claim 6 wherein the determining the safety status comprises determining whether the position is within one or more threshold deviations from a mean of the Bell curve.

10. The safety monitoring system of claim 1 wherein the plurality of sensors include:
 an infrared camera; and
 a 3-D camera; or
 an infrared camera and a 3-D camera.

11. The safety monitoring system of claim 1 wherein the stored information includes an initial data set and updating the stored information comprises adding data to the initial data set.

12. A method, comprising:
- receiving signals indicative of a current condition related to a safety status of a person;
- determining, using at least one processing device, the safety status of the person based on the signals indicative of the current condition and stored information related to the safety status of the person;
- updating, using the at least one processing device, the stored information related to the safety status of the person based on the signals indicative of the current condition; and
- when the determined safety status indicates the person may be in danger:
  - initiating one or more actions based on the determined safety status;
  - monitoring responses to the one or more initiated actions; and
  - updating the stored information related to the safety status of the person based on the monitored responses.

13. The method of claim 12 wherein the one or more initiated actions comprise:
- generating an alert signal to the person;
- transmitting a signal to a remote server;
- generating an alert message based on stored contact information; or
- combinations thereof.

14. The method of claim 12 wherein the signals indicative of the current condition include:
- a signal indicative of a location of the person;
- a signal indicative of a temperature;
- a signal indicative of a health status of the person;
- an imaging signal; or
- combinations thereof.

15. The method of claim 12 wherein the stored information comprises property identifiers indicative of conditions and the at least one processing device comprises an artificial intelligence module configured to compare the signals indicative of the current condition to the stored property identifiers and to determine the safety status of the person based on the comparison.

16. The method of claim 15 wherein the determining the safety status comprises determining a position of a property identifier on a characteristic Bell curve based on the at least one signal.

17. The method of claim 16 wherein the characteristic Bell curve is based on stored property identifiers indicative of the characteristic.

18. The method of claim 16 wherein the characteristic Bell curve is related to:
- an object identifier;
- a location identifier;
- a position identifier;
- a time identifier;
- a sound identifier;
- a motion identifier;
- a physical status identifier;
- an emotional identifier; or
- combinations thereof.

19. A non-transitory computer-readable medium whose contents configure a safety monitoring system to perform a method, the method comprising:
- receiving signals indicative of a current condition related to a safety status of a person;
- determining the safety status of the person based on the signals indicative of the current condition and stored information related to the safety status of the person;
- updating the stored information related to the safety status of the person based on the signals indicative of the current condition; and
- when the determined safety status indicates the person may be in danger:
  - initiating one or more actions based on the determined safety status;
  - monitoring responses to the one or more initiated actions; and
  - updating the stored information related to the safety status of the person based on the monitored responses.

20. A system, comprising:
- means for generating signals indicative of a current condition related to a safety status of a person;
- means for determining the safety status of the person based on the signals indicative of the current condition and stored information related to the safety status of the person;
- means for updating the stored information related to the safety status of the person based on the signals indicative of the current condition; and
- means for, when the determined safety status indicates the person may be in danger,
  - initiating one or more actions based on the determined safety status;
  - monitoring responses to the one or more initiated actions; and
  - updating the stored information related to the safety status of the person based on the monitored responses.

* * * * *